United States Patent
Sjoquist et al.

(10) Patent No.: US 12,354,750 B2
(45) Date of Patent: Jul. 8, 2025

(54) SELECTION OF A WEARABLE ARTICLE FOR A MEDICAL DEVICE

(71) Applicant: West Affum Holdings Corp, Grand Cayman (KY)

(72) Inventors: Steven E. Sjoquist, Lynnwood, WA (US); Mark P. Moore, Redmond, WA (US); Joseph L. Sullivan, Kirkland, WA (US); Jonathan P. Niegowski, Issaquah, WA (US); Hema A. Ingle, Woodinville, WA (US); Leo J. Gilbert, Kirkland, WA (US); Zoie R. Brent, Portland, OR (US)

(73) Assignee: West Affum Holdings DAC, Dublin (IE)

( * ) Notice: Subject to any disclaimer, the term of this patent is extended or adjusted under 35 U.S.C. 154(b) by 221 days.

(21) Appl. No.: 18/069,917

(22) Filed: Dec. 21, 2022

(65) Prior Publication Data

US 2023/0197273 A1   Jun. 22, 2023

Related U.S. Application Data

(60) Provisional application No. 63/293,016, filed on Dec. 22, 2021.

(51) Int. Cl.
*G16H 50/20* (2018.01)
*G06F 1/16* (2006.01)
*G16H 40/63* (2018.01)

(52) U.S. Cl.
CPC ............ *G16H 50/20* (2018.01); *G06F 1/163* (2013.01); *G16H 40/63* (2018.01)

(58) Field of Classification Search
CPC ......... G16H 50/20; G16H 40/63; G06F 1/163
See application file for complete search history.

(56) References Cited

U.S. PATENT DOCUMENTS 3,724,355 A    4/1973   Busch et al.
3,724,455 A    4/1973   Unger
(Continued)

FOREIGN PATENT DOCUMENTS

DE    102005060985 A2    6/2007
EP         2305110 A1    4/2011
(Continued)

OTHER PUBLICATIONS

Heartstart MRx and XL AED Algorithm—Application Note, Jul. 2001, Edition 2 Philips Healthcare, USA.
(Continued)

*Primary Examiner* — Michael I Ezewoko
(74) *Attorney, Agent, or Firm* — Lisa Benado; Propel IP Law, PLLC

(57) ABSTRACT

A medical wearable matching system is provided that pre-assesses a fit of a wearable article of medical device for a patient. The matching system may facilitate fitting and selection of a class of wearable articles for a patient. The matching system may also evaluate potential effects of the fit on operations of the medical device. Patient specific data, such as measurements, are fed into a fit prediction artificial intelligence ("AI") model. The fitting AI model is trained with fitting data of previous patients to predict a class of wearable medical article that is likely, above a threshold amount, to provide a target fit for the patient. The patient specific information may also be fed into an adverse potential AI model. The adverse potential AI model is trained with patient experience data describing adverse operations of a wearable article worn by prior patients.

17 Claims, 9 Drawing Sheets

(56) References Cited

U.S. PATENT DOCUMENTS

| | | |
|---|---|---|
| 4,583,524 A | 4/1986 | Hutchins |
| 4,619,265 A | 10/1986 | Morgan et al. |
| 4,666,432 A | 5/1987 | McNeish et al. |
| 4,698,848 A | 10/1987 | Buckley |
| 4,928,690 A | 5/1990 | Heilman et al. |
| 4,955,381 A | 9/1990 | Way et al. |
| 5,078,134 A | 1/1992 | Heilman et al. |
| 5,228,449 A | 7/1993 | Christ et al. |
| 5,348,008 A | 9/1994 | Bornn et al. |
| 5,353,793 A | 10/1994 | Bornn |
| RE34,800 E | 11/1994 | Hutchins |
| 5,394,892 A | 3/1995 | Kenny et al. |
| 5,405,362 A | 4/1995 | Kramer et al. |
| 5,429,593 A | 7/1995 | Matory |
| 5,474,574 A | 12/1995 | Payne et al. |
| 5,618,208 A | 4/1997 | Crouse et al. |
| 5,662,690 A | 9/1997 | Cole et al. |
| 5,708,978 A | 1/1998 | Johnsrud |
| 5,741,306 A | 4/1998 | Glegyak et al. |
| 5,782,878 A | 7/1998 | Morgan et al. |
| 5,792,204 A | 8/1998 | Snell |
| 5,902,249 A | 5/1999 | Lyster |
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,108,197 A | 8/2000 | Janik |
| 6,148,233 A | 11/2000 | Owen et al. |
| 6,201,992 B1 | 3/2001 | Freeman |
| 6,263,238 B1 | 7/2001 | Brewer et al. |
| 6,280,461 B1 | 8/2001 | Glegyak et al. |
| 6,287,328 B1 | 9/2001 | Snyder et al. |
| 6,304,780 B1 | 10/2001 | Owen et al. |
| 6,319,011 B1 | 11/2001 | Motti et al. |
| 6,334,070 B1 | 12/2001 | Nova et al. |
| 6,356,785 B1 | 3/2002 | Snyder et al. |
| 6,427,083 B1 | 7/2002 | Owen et al. |
| 6,437,083 B1 | 8/2002 | Brack et al. |
| 6,450,942 B1 | 9/2002 | Lapanashvili et al. |
| 6,529,875 B1 | 3/2003 | Nakajima et al. |
| 6,546,285 B1 | 4/2003 | Owen et al. |
| 6,546,309 B1* | 4/2003 | Gazzuolo ............... G06T 17/20 <br> 702/167 |
| 6,671,545 B2 | 12/2003 | Fincke |
| 6,681,003 B2 | 1/2004 | Linder et al. |
| 6,762,917 B1 | 7/2004 | Verbiest et al. |
| 7,065,401 B2 | 6/2006 | Worden |
| 7,099,715 B2 | 8/2006 | Korzinov |
| 7,194,327 B2* | 3/2007 | Lam ..................... A41H 3/007 <br> 700/134 |
| 7,212,850 B2 | 5/2007 | Prystowsky |
| 7,346,421 B2* | 3/2008 | Bijvoet .................. A41H 3/007 <br> 700/130 |
| 7,559,902 B2 | 7/2009 | Ting et al. |
| 7,587,237 B2 | 9/2009 | Korzinov |
| 7,753,759 B2 | 7/2010 | Pintor et al. |
| 7,865,238 B2 | 1/2011 | Brink |
| 7,870,761 B2 | 1/2011 | Valentine et al. |
| 7,907,996 B2 | 3/2011 | Prystowsky |
| 7,941,207 B2 | 5/2011 | Korzinov |
| 7,974,689 B2 | 7/2011 | Volpe et al. |
| 8,135,462 B2 | 3/2012 | Owen et al. |
| 8,140,154 B2 | 3/2012 | Donnelly et al. |
| 8,369,944 B2 | 2/2013 | Macho et al. |
| 8,478,663 B2* | 7/2013 | Lu ...................... G06Q 30/0631 <br> 705/26.7 |
| 8,527,028 B2 | 9/2013 | Kurzweil et al. |
| 8,548,557 B2 | 10/2013 | Garstka et al. |
| 8,560,044 B2 | 10/2013 | Kurzweil et al. |
| 8,615,295 B2 | 12/2013 | Savage et al. |
| 8,644,925 B2 | 2/2014 | Volpe et al. |
| 8,676,313 B2 | 3/2014 | Volpe et al. |
| 8,706,255 B2 | 4/2014 | Phillips et al. |
| 8,742,349 B2 | 6/2014 | Urbon et al. |
| 8,762,292 B2* | 6/2014 | Bright .................. G06Q 10/04 <br> 705/347 |
| 8,897,860 B2 | 11/2014 | Volpe et al. |
| 8,904,214 B2 | 12/2014 | Volpe et al. |
| 8,965,500 B2 | 2/2015 | Macho et al. |
| 9,008,801 B2 | 4/2015 | Kaib et al. |
| 9,084,583 B2 | 7/2015 | Mazar et al. |
| 9,089,685 B2 | 7/2015 | Sullivan et al. |
| 9,119,547 B2 | 9/2015 | Cazares et al. |
| 9,131,901 B2 | 9/2015 | Volpe et al. |
| 9,132,267 B2 | 9/2015 | Kaib |
| 9,265,432 B2 | 2/2016 | Warren et al. |
| 9,345,898 B2 | 5/2016 | Piha et al. |
| 9,408,548 B2 | 8/2016 | Volpe et al. |
| 9,445,719 B2 | 9/2016 | Libbus et al. |
| 9,454,219 B2 | 9/2016 | Volpe et al. |
| 9,579,020 B2 | 2/2017 | Libbus et al. |
| 9,592,403 B2 | 3/2017 | Sullivan |
| 9,598,799 B2 | 3/2017 | Shoshani et al. |
| 9,675,804 B2 | 6/2017 | Whiting et al. |
| 9,724,008 B2 | 8/2017 | Sullivan et al. |
| 9,878,171 B2 | 1/2018 | Kaib |
| 9,895,105 B2 | 2/2018 | Romem |
| 9,901,741 B2 | 2/2018 | Chapman et al. |
| RE46,926 E | 7/2018 | Bly et al. |
| 10,076,656 B2 | 9/2018 | Dar et al. |
| 10,192,387 B2 | 1/2019 | Brinig et al. |
| 10,307,133 B2 | 6/2019 | Kaib |
| 10,463,867 B2 | 11/2019 | Kaib et al. |
| 10,589,110 B2 | 3/2020 | Oskin et al. |
| 10,599,814 B2 | 3/2020 | Landrum et al. |
| 10,621,779 B1* | 4/2020 | Topiwala ............. G06F 18/253 |
| 10,664,903 B1* | 5/2020 | Haitani ................ G02B 27/017 |
| 10,984,342 B2* | 4/2021 | Yu ............................ G06N 7/01 |
| 11,062,377 B1* | 7/2021 | Piroska ............. G06Q 30/0631 |
| 11,080,727 B1* | 8/2021 | Novak ................... G06N 20/00 |
| 11,100,560 B2* | 8/2021 | Parker ............... G06Q 30/0603 |
| 11,144,845 B2* | 10/2021 | Boyle ...................... G06N 5/04 |
| 11,232,506 B1* | 1/2022 | Zielnicki ............ G06Q 30/0631 |
| 11,669,776 B2* | 6/2023 | Boyle ................. G06Q 10/067 <br> 706/12 |
| 11,734,747 B2* | 8/2023 | Zielnicki ............ G06Q 10/083 <br> 705/26.7 |
| 11,983,748 B2* | 5/2024 | Foley ..................... G06N 20/20 |
| 2002/0181680 A1 | 12/2002 | Linder et al. |
| 2003/0158593 A1 | 8/2003 | Heilman et al. |
| 2005/0107833 A1 | 5/2005 | Freeman et al. |
| 2005/0107834 A1 | 5/2005 | Freeman et al. |
| 2006/0173499 A1 | 8/2006 | Hampton et al. |
| 2008/0255920 A1* | 10/2008 | Vandergriff ........ G06Q 30/0601 <br> 705/26.1 |
| 2008/0312709 A1 | 12/2008 | Volpe et al. |
| 2009/0005827 A1 | 1/2009 | Weintraub et al. |
| 2010/0007413 A1 | 1/2010 | Herleikson et al. |
| 2010/0023421 A1* | 1/2010 | Wannier ................ G06Q 30/06 <br> 705/26.1 |
| 2010/0111370 A1* | 5/2010 | Black .................. G06F 18/2321 <br> 705/26.1 |
| 2010/0298899 A1 | 11/2010 | Donnelly et al. |
| 2011/0022105 A9 | 1/2011 | Owen et al. |
| 2011/0083331 A1* | 4/2011 | Hopman ................. A41H 1/02 <br> 33/2 R |
| 2011/0099122 A1* | 4/2011 | Bright ................ G06Q 10/067 <br> 705/348 |
| 2011/0231278 A1* | 9/2011 | Fries ................. G06Q 30/0621 <br> 705/26.5 |
| 2011/0288604 A1 | 11/2011 | Kaib et al. |
| 2011/0288605 A1 | 11/2011 | Kaib et al. |
| 2012/0112903 A1 | 5/2012 | Kaib et al. |
| 2012/0144551 A1 | 6/2012 | Guldalian |
| 2012/0150008 A1 | 6/2012 | Kaib et al. |
| 2012/0158075 A1 | 6/2012 | Kaib et al. |
| 2012/0191476 A1 | 7/2012 | Reid et al. |
| 2012/0265265 A1 | 10/2012 | Razavi et al. |
| 2012/0283794 A1 | 11/2012 | Kaib et al. |
| 2012/0293323 A1 | 11/2012 | Kaib et al. |
| 2012/0302860 A1 | 11/2012 | Volpe et al. |
| 2012/0310315 A1 | 12/2012 | Savage et al. |

(56) References Cited

U.S. PATENT DOCUMENTS

| | | | |
|---|---|---|---|
| 2013/0066750 A1* | 3/2013 | Siddique | G06Q 20/12 705/27.2 |
| 2013/0083065 A1* | 4/2013 | Schulze | G06Q 30/06 345/633 |
| 2013/0085538 A1 | 4/2013 | Volpe et al. | |
| 2013/0144355 A1 | 6/2013 | Macho et al. | |
| 2013/0231711 A1 | 9/2013 | Kaib | |
| 2013/0245388 A1 | 9/2013 | Rafferty et al. | |
| 2013/0274565 A1 | 10/2013 | Langer et al. | |
| 2013/0317852 A1 | 11/2013 | Worrell et al. | |
| 2013/0325078 A1 | 12/2013 | Whiting et al. | |
| 2014/0012144 A1 | 1/2014 | Crone | |
| 2014/0025131 A1 | 1/2014 | Sullivan et al. | |
| 2014/0040041 A1* | 2/2014 | Ohnemus | G06Q 30/0643 705/14.66 |
| 2014/0046391 A1 | 2/2014 | Cowan et al. | |
| 2014/0070957 A1 | 3/2014 | Longinotti-Buitoni et al. | |
| 2014/0163663 A1 | 6/2014 | Poddar et al. | |
| 2014/0244431 A1* | 8/2014 | Bright | G06Q 30/0631 705/26.7 |
| 2014/0324112 A1 | 10/2014 | Macho et al. | |
| 2014/0358738 A1* | 12/2014 | Ohnemus | G06Q 30/0601 705/27.2 |
| 2014/0378812 A1 | 12/2014 | Saroka et al. | |
| 2015/0039053 A1 | 2/2015 | Kaib et al. | |
| 2015/0161554 A1 | 6/2015 | Sweeney et al. | |
| 2015/0297135 A1 | 10/2015 | Shoshani et al. | |
| 2015/0328472 A1 | 11/2015 | Sullivan et al. | |
| 2016/0004831 A1 | 1/2016 | Carlson et al. | |
| 2016/0005070 A1* | 1/2016 | Burr | G06Q 30/0253 705/14.51 |
| 2016/0076175 A1 | 3/2016 | Rock et al. | |
| 2016/0076176 A1 | 3/2016 | Rock et al. | |
| 2016/0082277 A1 | 3/2016 | Foshee, Jr. et al. | |
| 2016/0113581 A1 | 4/2016 | Amir et al. | |
| 2016/0256104 A1 | 9/2016 | Romem et al. | |
| 2016/0283900 A1 | 9/2016 | Johnson et al. | |
| 2016/0292765 A1* | 10/2016 | Jin | G06Q 30/0629 |
| 2017/0014073 A1 | 1/2017 | Shoshani et al. | |
| 2017/0027469 A1 | 2/2017 | Amir et al. | |
| 2017/0036066 A1 | 2/2017 | Chahine | |
| 2017/0039622 A1* | 2/2017 | Chen | G06Q 30/0201 |
| 2017/0040758 A1 | 2/2017 | Amir et al. | |
| 2017/0162840 A1 | 6/2017 | Pendry | |
| 2017/0273383 A1* | 9/2017 | deGuzman | G06Q 30/0641 |
| 2017/0319862 A1 | 11/2017 | Foshee, Jr. et al. | |
| 2017/0367591 A1 | 12/2017 | Jorgensen | |
| 2018/0116537 A1 | 5/2018 | Sullivan et al. | |
| 2018/0117299 A1 | 5/2018 | Gustavson et al. | |
| 2018/0184933 A1 | 7/2018 | Sullivan et al. | |
| 2018/0185662 A1 | 7/2018 | Foshee, Jr. et al. | |
| 2018/0243578 A1 | 8/2018 | Volosin | |
| 2018/0349795 A1* | 12/2018 | Boyle | G06Q 10/067 |
| 2018/0361165 A1 | 12/2018 | Jaax et al. | |
| 2019/0030352 A1 | 1/2019 | Sullivan et al. | |
| 2019/0073335 A1* | 3/2019 | Foley | G06V 40/10 |
| 2019/0076666 A1 | 3/2019 | Medema | |
| 2019/0108458 A1* | 4/2019 | Yu | A41H 43/00 |
| 2019/0116896 A1 | 4/2019 | Armour et al. | |
| 2019/0321650 A1 | 10/2019 | Raymond et al. | |
| 2020/0302506 A1* | 9/2020 | Parker | G06Q 30/0631 |
| 2020/0320769 A1* | 10/2020 | Chen | G06F 18/214 |
| 2021/0209510 A1* | 7/2021 | Yu | G06N 7/01 |
| 2021/0326913 A1* | 10/2021 | Novak | G06Q 30/0631 |
| 2022/0054848 A1 | 2/2022 | Szul | |
| 2022/0058526 A1* | 2/2022 | Boyle | G06Q 10/067 |
| 2022/0092672 A1* | 3/2022 | Zielnicki | G06Q 10/083 |
| 2022/0257959 A1 | 8/2022 | Sullivan | |

FOREIGN PATENT DOCUMENTS

| | | |
|---|---|---|
| JP | 2005507747 A | 3/2005 |
| JP | 2014500099 A | 1/2014 |
| JP | 2014526282 A2 | 10/2014 |
| WO | 9839061 A1 | 9/1998 |
| WO | 2011/146448 A1 | 11/2011 |
| WO | 2012/064604 A1 | 5/2012 |
| WO | 2012/151160 A1 | 11/2012 |
| WO | 2015/056262 A1 | 4/2015 |
| WO | 2023107404 A2 | 6/2023 |

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

Lifecor LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Pagan-Carlo, et al., "Encircling Overlapping Multipulse Shock Waveforms for Transthoracic Defibrillation," JACC Journals, Dec. 1998, vol. 32 Issue 7, p. 2065-2071.

The LifeVest Network/Patient Data Management System, Zoll, 2015, 2000503 Rev A.

Zoll, LifeVest, Proven protection from Sudden Cardiac Death, issued Mar. 27, 2018, 4 pages. Pittsburgh PA, USA.

International Search Report and Written Opinion for PCT Application No. PCT/US2015/051726, dated May 20, 2016, European Patent Office, Rijswijk, 11 pages.

* cited by examiner

SELECTION OF A WEARABLE ARTICLE FOR A MEDICAL DEVICE

CROSS REFERENCES TO RELATED APPLICATIONS

This application claims the benefit of the filing date of U.S. Provisional Patent Application No. 63/293,016, filed Dec. 22, 2021, the disclosure of which is hereby incorporated herein by reference for all purposes.

This application is related to U.S. patent application Ser. No. 16/946,512, filed on Jun. 24, 2020 and U.S. patent application Ser. No. 17/163,099, filed on Jan. 29, 2021, both of which are hereby incorporated by reference as if set forth in full in this application for all purposes.

FIELD OF THE INVENTION

The present disclosure generally relates to fitting and matching of wearable medical devices for patients.

BACKGROUND

Various medical devices worn by a patient gather health related data while the patient goes about day-to-day activities. It can be important for wearable medical devices to fit on a patient in a manner that allows for proper functioning.

Certain medical devices detect and provide critical health information that may require immediate attention, such as lifesaving alerts of cardiac conditions. For example, medical devices used in cardiac monitoring may have electrocardiogram (ECG) electrodes that detect electrical impulses of the heart. Sensors on medical devices need to be situated in appropriate positions on or near the patient so that accurate data may be acquired. Some wearable devices also provide treatment on the fly. Often the treatment needs to be provided at specific points in the body. Extended wear medical devices need to allow sensors to remain in place as the wearable accommodates patient movement. The wearable device should also fit in a manner that avoids excessive discomfort for the patient.

To achieve proper fit of wearable medical devices, a patient often tries on the wearable in an in-person setting. Some patients may have difficulty traveling to locations that house the wearable to try them on. A representative (also referred to as "agent") may bring samples of the wearables to the patient to determine an accurate fit for the patient. The representative may select the appropriate wearable by personal observations of the patient and manual physical measurements, such as taking an underbust measurement with a tape measure. The visiting representative often needs to carry multiple styles and sizes of the wearables to the patient for proper selection after the physical assessment.

SUMMARY

A present medical wearable matching system (also referred to as a "matching system") is provided to facilitate selection and use of a wearable medical article (also referred to as "wearable article" or "wearable") of a medical device. The fit of the wearable article on a patient can affect the performance of the medical device such as detection of a medical condition and/or a therapeutics to treat a medical condition.

The matching process performed by the medical wearable matching system includes receiving patient specific data including body measurement data. Predictive analysis is conducted using a first artificial intelligence ("AI") model to predict a class (also known as a group or category) of a wearable article that provides a target fit for a patient. The predictive analysis is based, at least in part, on the patient specific data as input to the first AI model. The first AI model is trained using fitting data of previous patients. The class of the wearable article is selected by the matching system based, at least in part, on an output result of the predictive analysis.

One or more capture devices may be used to obtain body measurement data as patient specific data. The one or more capture devices may be selected from a group of devices including a Light Detection and Ranging (LiDAR) device, a body scanner, a camera, a digital scale, and combinations thereof.

The patient specific data used in the matching process may include, in addition to the bode measurement data, one or more of a patient medical condition, a patient lifestyle descriptor, body variation information, or patient preference information. Further, a target fit that the matching process seeks to achieve in the selection of wearable article may be based, at least in part, on fit factors for wearable component-to-body positioning for performance of the medical device.

According to some implementations, a local client computing device, such as a patient mobile device and/or one or more remote computing devices, such as servers accessible to the client computing device, may perform various tasks of the matching process. Other computing devices and/or storage devices may also be employed. For example, at least a portion of the patient specific data may be obtained by a local client computing device and transferred to a remote computing device. The remote computing device may conduct the predictive analysis described herein and select the class of the wearable article for the patient. In some implementations, the predictive analysis may be conducted by a remote computing device and the output result of the AI model of the remote computing device is received by a client computing device. The client computing device may then select the class of the wearable article. In still some implementations, at least a portion of the patient specific data may be obtained by a local client computing device, which then conducts the predictive analysis and selects the class of the wearable article without participation from the remote computing device.

In some implementations, a second predictive analysis is conducted using a second AI model to predict an adverse fit potential of the selected wearable article. The second predictive analysis may be based on the patient specific data and the selected class of the wearable article as inputs to the second AI model. The second AI model may be trained using patient experience data.

In some implementations, as a pool of available fitting data increases, the first AI model may be retrained with updated inputs including additional fitting data for new patients fitted with the wearable article. Retraining of the first AI model may also occur by feeding discrepancy information back into the first AI model. Such discrepancy information may include at least one of patient survey information or replacement data for replacement of previously wearable articles predicted by the first AI model to provide target fit for previous patients.

In some aspects, a matching system may be provided for automatic selection of a wearable article of a medical device system. Such matching system may include at least one computing device comprising various components including an interface for receiving patient specific data, such as body measurement data. One or more processors may be provided in the computing device(s), including logic encoded in one or more non-transitory media for execution by the one or more processors and when executed, it is operable to perform certain steps. Such steps may comprise conducting predictive analysis using a first AI model to predict a class of wearable article that provides a target fit for a patient based, at least in part, on the patient specific data as input to the first AI model. The first AI model may be trained using fitting data of previous patients. The steps may further include selecting the class of the wearable article based, at least in part, on an output result of the predictive analysis. With some matching systems, the body measurement data may be obtained by use of one or more capture devices selected from the group of: a LiDAR device, a body scanner, a camera, a digital scale, and combinations thereof.

According to some implementation of the matching system, a local client computing device and remote computing device are employed. The client computing device may be configured to obtain at least a portion of the patient specific data and also transfer the data to the remote computing device. The remote computing device may be configured to conduct the predictive analysis and to select the class of the wearable article.

In still some configurations, the remote computing device of the system may be configured to conduct the predictive analysis. The local client computing device may be configured to receive the output result from the remote computing device and to select the class of the wearable article.

In other implementations, the local client computing device may be configured to obtain at least a portion of the patient specific data at a patient location and transfer the at least portion of the patient specific data to the remote computing device. In these cases, the remote computing device is employed to conduct predictive analysis. Output results of the analysis may be transferred back to the client computing device, which uses the analysis results to select the class of the wearable article.

Some matching systems may also include a second AI model to conduct a second predictive analysis that predicts an adverse fit potential of the selected wearable article. The patient specific data and the selected class of the wearable article may be used as inputs to the second AI model. The second AI model may be trained using patient experience data. The processor of the system may further comprise logic to retrain the first AI model with updated inputs including additional fitting data for new patients fitted with the wearable article.

In various implementations, a method is provided for automatically selecting a wearable article of a medical monitoring device for a patient. The method includes training a first AI model using fitting data of previous patients to predict a class of the wearable article that provides a target fit for a patient. Patient specific data including body measurement data of a patient is received and inputted into the trained first AI model. Predictive analysis is conducted using the trained first AI model to predict a class of a wearable article that provides a target fit for a patient based, at least in part, on the patient specific data as input to the trained first AI model. The class of the wearable article is selected based, at least in part, on an output result of the predictive analysis. It may then be determined whether the selected class of the wearable article provides the target fit for the patient. If the selected class of the wearable article fails to provide the target fit, discrepancy data may be generated to feed back into the first AI model for retraining.

In some implementations of the method, it may be determined that additional fitting data for new patients fitted with the wearable articles are available. The trained first AI model may be retrained with the additional fitting data.

According to the method, a second AI model may be trained using patient experience data of previous patients to predict an adverse fit potential of the selected wearable article. The patient specific data may be inputted into the trained second AI model. A second predictive analysis may be conducted using the trained second AI model to predict the adverse fit potential of the selected wearable article. The prediction of the adverse fit potential may be based on the patient specific data and the selected class of the wearable article class. It may be determined whether the selected class of the wearable article causes an adverse experience for the patient. If the selected class of the wearable article causes an adverse experience, discrepancy data may be generated to feed back into the trained second AI model for retraining.

BRIEF DESCRIPTION OF THE DRAWINGS

Various implementations in accordance with the present disclosure will be described with reference to the drawings.

FIGS. 6A and 6B are schematic diagrams of examples of various vest-type styles of wearable articles worn on patients, in which FIG. 6A shows a first style wearable article, and FIG. 6B shows a second style wearable article, in accordance with some implementations.

DETAILED DESCRIPTION

Figure 1:
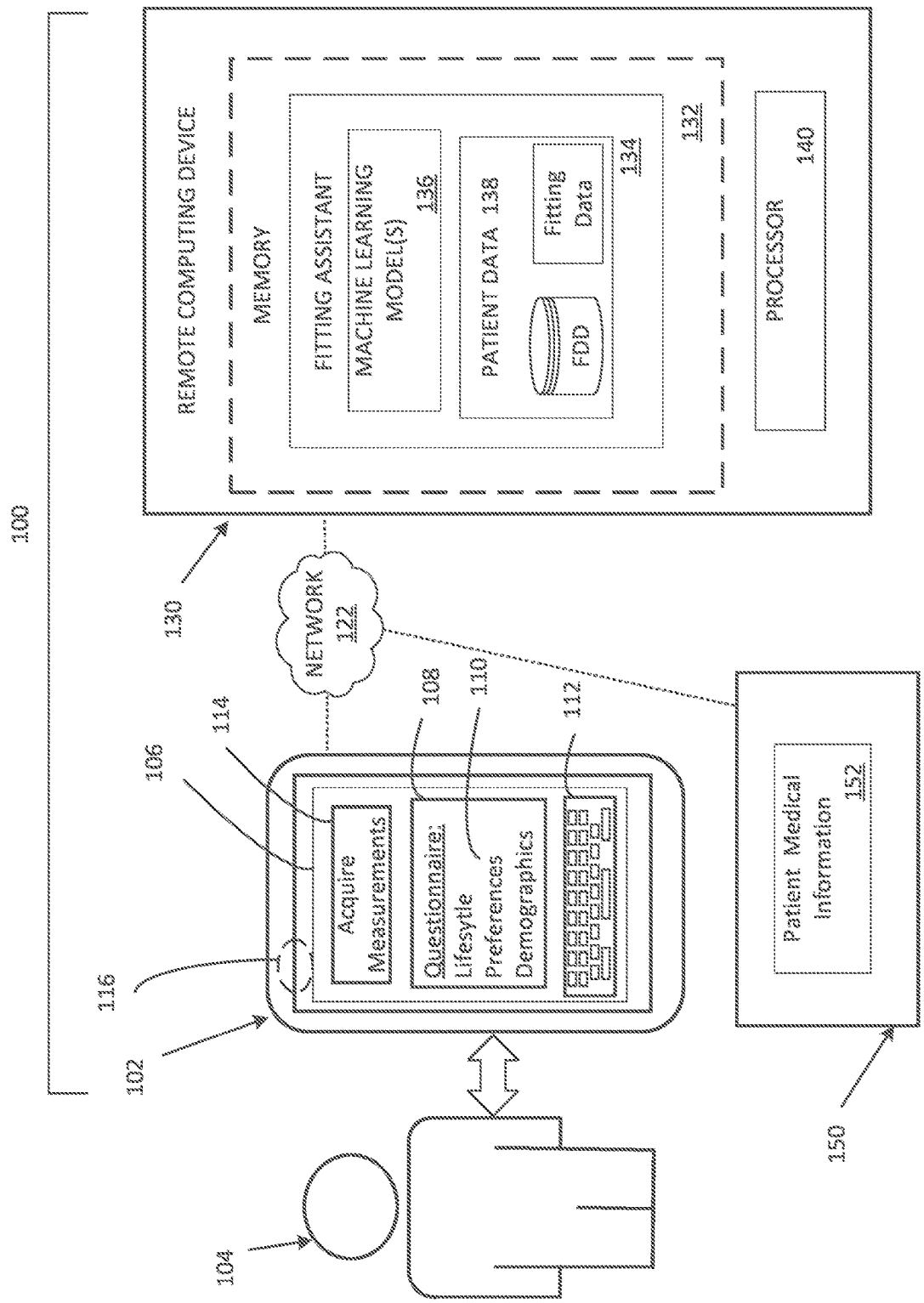
FIG. 1 is a diagram of an example medical wearable matching system, in accordance with some implementations.

In the following description, various implementations will be described. For purposes of explanation, specific configurations and details are set forth in order to provide a thorough understanding of the implementations. However, it will also be apparent to one skilled in the art that the implementations may be practiced without the specific details. Well-known features may be omitted or simplified without obscuring the implementations described. The description of the medical wearable matching system provides a framework which can be tailored to individual systems built around the medical wearable matching system. Elements may be described in terms of "basic functionality" or varying degrees of functionality.

The present medical wearable matching system ("matching system") performs a pre-assessment of the potential fit of a wearable article of medical device for a patient. The process facilitates fitting and selection of a class of wearable articles for a patient. The matching system may also evaluate possible effects of the fit on operations of the medical device. The process relies upon patient data obtained from various sources.

The matching process can be based on characteristics of a patient, such as height, weight, sex, demographics, medical conditions, photos, videos, Light Detection and Ranging (LiDAR or Lidar or lidar) images, wearer/patient feedback, etc. These inputs can be used alone or in combination to allow more flexibility in use. Data collected over a population of successfully fitted and/or unsuccessfully fitted patients can supplement individual patient inputs allowing a matching process to more accurately determine a style and size of wearable article that best fits the patient.

In one example, a client computing device, such as a mobile device, does not have Internet access to a remote computing device. The offline client device may be limited to use a subset of locally collected data in performing the matching process due to low computing power that may be required to process a more comprehensive dataset with multimedia data. In another example, a connected client computing device can use local processing of the client computing device and cloud-based algorithms which can employ an expanded set of inputs such as images, videos, and lidar images to determine the best fit.

Artificial intelligence (AI) techniques, for example machine learning (ML), can be used according to the matching system to select a wearable article, e.g., a garment, based on inputs. The inputs can include various aspects of patients and/or data associated with patients across a large and growing population of previously fitted patients. As more input data and actual wearable selection results are collected, AI models may be updated and provide more predictive accuracy for output results based on new sets of patient data.

The wearable article may be a component of a medical device, or the wearable article may be all inclusive in which the wearable article integrates the functionality required to provide medical monitoring and/or care to the patient. The term, "medical device" as used herein refers to one or more physical devices and/or software components.

The present matching system provides patient specific data that is fed into a fitting artificial intelligence ("AI") model using a specific fitting algorithm ("SFA") that runs on a client computing device and/or historical fitting algorithm (HFA) that runs on one or more remote computing devices. It should be understood that the fitting AI model as described below can use either or both SFA and HFA algorithms.

In some implementations, the HFA at the remote computing device outputs a candidate for the wearable article selection and the candidate wearable article is communicated to the SFA at the client computing device, which, in some implementations, can perform a separate SFA determination. The HFA output and SFA determination may be combined to select a class of wearable article by the client computing device.

The SFA typically relies on specifics of a particular patient as a narrow dataset compared to HFA, which uses a broad dataset, to select a class of wearable article having a particular style and size for a specific patient. The HFA calculations are based on determining a relationship of the patient to a stored population of patients and previous selections/results. In some embodiments, the HFA also uses multiple factor analysis to select a class of wearable article (having a particular style and size) to best fit the specific patient.

The fitting AI model is trained with fitting data of previous patients to predict a class of wearable article that is likely, above a predefined threshold level, to provide a target fit for the patient. The target fit includes one or more predetermined factors for the fit of the wearable to enable optimal performance of the medical device.

In some implementations of the medical wearable matching system, the patient specific information is fed into an adverse potential AI model. The adverse potential AI model is trained with patient experience data describing suboptimal operations of a wearable article worn by prior patients, in which a poorly functioning medical device was due, at least in part, to the fit of a class of wearable article on the patient.

In some implementations, the medical device may be a medical monitoring device to monitor the patient for medical condition(s) and/or a medical treatment device to provide medical treatment to the patient.

The fit of a wearable medical article on a patient can have a direct or an indirect effect on performance of the medical device. For example, where an ill-fitted wearable article results in poor sensor to body connection, data acquired by the sensor may be skewed and health events may be missed. For wearable medical devices that provide treatment to a patient, improper positioning of treatment contact points of the wearable on the body may compromise the treatment of the patient.

Performance of the medical device may also be indirectly affected by an ill-fitting wearable article if a patient fails to comply with use requirements due to discomfort. Comfort may be especially significant for extended wear medical device that is worn continuously, for example, fourteen (14) or more days. A patient may fail to wear the wearable article if, for example, the wearable article is too small, too big, sensors dig into the patient, or there are other problems associated with the fit. To facilitate compliance by the patient with the extended wear regimen, the wearable article should fit comfortably on the patient.

Different classes of wearable medical articles from which the matching system selects for a patient, may include various combinations of styles and sizes of the wearable article. Styles of wearable medical articles may have distinct arrangements of components and/or features, cover different body parts, or other variations that may affect the fit of the wearable article on a body. In some example, styles of the wearable article can include designs for patients with breasts, designs for patients without breasts, vest styles, t-shirt styles, etc. Various classes of wearable articles typically include different features that affect the fit and potentially can impact the operation of the medical device, rather than groupings of wearable articles that provide solely esthetic variations, e.g., colors, fabric patterns, etc.

Fit of the wearable article refers to how the article engages with a part of the patient's body, such as according to a size and/or style of the wearable article. A target fit is assumed to provide a required fit for the medical device to operate effectively. The target fit may include a combination of factors that together meet a predefined threshold level, some factors of which may be weighted more than other factors. Fit factors may include particular patient body measurements or a range of body measurements, sensor-to-body contact at a particular location of the body and sufficient contact with the body, patient comfort level, such as, according to a numerical scale, descriptive word ratings, emojis signifying comfort levels, or other mechanisms to assess comfort level, and other fit factors relevant to distinguish a target fit.

The AI models use AI algorithms, such as in the machine learning domain including classification and/or regression, to learn from the training data and apply the learning to conduct various prediction tasks. For example, a fitting AI model calculates a class of wearable articles that is predicted to provide a target fit for a particular patient. An adverse fit potential AI model may predict that an unfavorable event is more probable than not to be experienced by the patient wearing a particular selected wearable article.

In an example use case of the medical wearable matching system, an illustrative patient seeks treatment from a medical provider for cardiac episodes that she experiences. The illustrative patient is prescribed an extended wear medical device to wear on the torso continuously for at least fourteen days to monitor heart function. The medical device includes a vest-type wearable article available in various sizes and styles that fit on a patient in different ways. The illustrative patient wears the wearable medical monitoring system during her day-to-day routines as well as through the night. The wearable article provider needs to select a wearable article that fits the illustrative patient in a manner that optimizes performance of the wearable article, is comfortable for the illustrative patient to continuously wear, and minimizes additional stress on the patient from wearing the wearable article for an extended time.

The illustrative patient downloads a client fitting application on a mobile phone. The application provides a graphical user interface (GUI) that is rendered on the mobile phone display and prompts the illustrative patient to enter patient specific data. The illustrative has the option of opening a body measurement feature of the mobile phone, such as a built in Light Detection and Ranging (LiDAR, or Lidar, or lidar) scanner. In some implementations, the illustrative patient can control the LiDAR scanner within the client fitting application. In other implementations, the illustrative patient can take body measurements independent of the client fitting application, such as with other mobile phone applications or other devices, and manually enter the measurement data into the client fitting application.

In this use case example, the illustrative patient selects a start scanning control element on the GUI and stands at an appropriate distance and body position from mobile device. The LiDAR scanner detects the height, bust girth, underbust measurement, and waist size of the patient. The body measurement data is extracted from the scans for use by the client fitting application. The illustrative patient is also instructed to turn around 360 degrees while the mobile phone captures a video of the patient, from which additional information is extracted regarding body shape. The illustrative patient uses a separate scale device to measure body weight and enters the data into the client fitting application. The GUI displays a questionnaire with questions for the illustrative patient to enter answers. Questions include demographics (such as gender, age, etc.), preferences of style, lifestyle descriptors, requests for other body variations, such as wheelchair bound, loss of limbs, limitations on use, accommodations for use of other medical devices, etc. The illustrative patient may also enter permission for the client fitting application to access medical records, such as medical condition information from an external source, such as a healthcare provider or medical data storage device.

Upon completing the entering of the patient specific data, the GUI displays the selected class of wearable article chosen for the illustrative patient. The selection of the class of wearable article works in the background with use of one or more fitting AI models and the selection appears immediate and seamless to the representative patient. The selected class is transmitted to a representative who coordinates with the illustrative patient.

The illustrative patient can opt to have the selected wearable article shipped to a convenient location or have the representative deliver the selected wearable article to the illustrative patient for trying on. In this use case example, the representative schedules a time to bring the selected class of wearable article to the illustrative patient to try on, ensure proper fit, and to train the patient on use. The representative only needs to provide the selected class of wearable article, or perhaps a couple of back up similar wearable articles to the appointment with the illustrative patient. The illustrative patient tries on the selected class of wearable article and finds the wearable article comfortable. The extended and continuous wear is easy without the illustrative patient needing to remember to put it on, which may occur with other recreational-use health monitors, such as health features in smartwatches and activity trackers.

The matching system has also flagged a potential future problem that the patient may experience with the recommended class of wearable device. The matching system conducts an evaluation of a potential for future adverse fit using an adverse detection application with an adverse fit potential AI model. The matching system determines there is an actionable adverse potential for future misfitting of the selected class of wearable article based on the illustrative patient having a history of fluctuating weight and/or current participation in a diet plan. The history information may have been obtained by the patient questions or retrieval of medical records. The alert is provided to the illustrative patient and the healthcare provider of the patient. The illustrative patient may be monitored for future weight change above a threshold amount during the period of using the wearable article. Above the threshold amount of weight gain or loss require reselection of a class of wearable article.

The medical wearable matching system is not limited to the described use case. As can be recognized by the description herein, there are numerous other situations in which the medical wearable matching system may be employed to select a wearable article with proper patient fit and/or evaluate fit for predictive adverse effects.

By comparison to the present matching process by the medical wearable matching system, other processes to fit a patient with a wearable device require in-person appointments to take measurements and put on the wearable. Current processes often requires a representative to bring numerous samples of wearable articles to the appointments. The wearable articles can be bulky and it can be burdensome for the representative to carry the many available classes of the wearable articles to each appointment.

The present matching system enables selection of the wearable article remotely without requiring a representative to be physically present to take patient measurements. The patient may avoid needing to try on multiple versions of the wearable article. In some implementations, a proper style and size of garment can be selected and shipped to the patient without in-person contact. In some implementations, after a class of wearable article is selected, a representative can opt to bring just the proper wearable article or optionally a couple of additional variations as backups to the patient. The matching system can provide a better user experience with less time used for fitting the patient, a reduction of cost due to not needing many samples of wearable articles, and convenience for both the patient and representative, especially for patients who are less mobile. The remote fitting process may also include providing the patient with remote patient instructions on use of the medical device, such as how to put it on, how to activate, how to trouble shoot, etc. The matching process can be applied to multiple wearable medical devices, resulting in cost effective increase in scalability.

Often times, problems with a fit of a wearable medical device are not detected until actual use. With the present matching system, predicting potential issues with the operation of the medical device related to fit of the wearable article may save time and cost in replacing a wearable article. Predicting potential future problems can lead to improved patient satisfaction with the wearable device and improved operation effectiveness to provide for improved medical care of the patient. In some implementations, the adverse potential prediction process may be employed at the initial selection of the wearable article as additional patient data for improved selection.

Other benefits of the matching system will be apparent from the further description of the system and methods, as described below.

FIG. 1 shows an overview of an example of the medical wearable matching system 100 that employs a local client computing device 102 of a current patient 104 that may be in communication across a network 122 with a remote computing device 130 (which may be collectively one or more remote computing devices) located away from the location of the client computing device. The remote computing device 130 may also be in communication with a patient medical information source 150.

The client computing device may be a local device in a location that is at or near the patient. The client computing device, such as a mobile device, e.g., a smart phone, tablet or other personal device, may be controlled by the patient, a residential caretaker of the patient, friend or relative of the patient, or other similar persons.

The client computing device 102 may be used to acquire at least a portion of patient specific data collected by a fitting application and used for predictive analysis. The patient specific data may include objective or subjective data regarding the patient, which can be manually entered, measured by devices, extracted from photos or videos, etc. Such patient specific data may include body measurements (as described below with regard to FIG. 2), demographics, gender, medical condition(s), etc. Other patient specific data can include body variation information (e.g., differences from typical bodies caused by injury, birth defects, surgery, etc.), body shape, hot spots (due to garment friction or being too tight), mobility (e.g., wheelchair bound), posture, gait, visible physical or medical idiosyncrasies, or atypical body contours, etc.

Other subjective data may include preferences, such as preferred style or size of wearable article, patient lifestyle descriptors, such as athletic, generally sedentary, etc. Some other impacting factors may include personality, temperament, psychological conditions, touch sensitivities, etc., compliance information such as an ability of patient to put on or take off wearable article, etc.

The client computing device 102 may receive patient specific data using a variety of data collection mechanisms. Some sensor devices may be integrated in the client computing device, such as cameras for photos and/or videos, a LiDAR scanner, an infrared sensor for thermal imaging, etc. External sensor devices such as a scale, body fat sensor, may be wired or wirelessly connected to the client computing device to provide measurement data.

The client computing device 102 displays a GUI 106 for user interaction with the fitting application running a specific fitting algorithm (SFA) installed in the client computing device 102 and/or an adverse detection application. In some implementations, the GUI may also allow the user to interact with a fitting applications running a historical fitting algorithm (HFA) at the remote computing device, and/or adverse detection application running on the remote computing device of the matching system. In some implementations, the remote computing device includes one or more servers implemented in the cloud and is referred to herein as the Cloud Computing Processor (CCP).

The GUI 106 may enable the patient 104 to enter patient specific data on a questionnaire 108 portion of the GUI 106 using various user input mechanisms. User inputs: keyboard 112 including alphanumeric and other keys to enter text or activate control functions. In some implementations, a user contacts the display screen using a finger or stylus in order to select items displayed by the display screen.

The client computing device 102 may accept various other inputs, such as, without limitation, audio, e.g. voice recognition, touchscreen, switch input with an on-screen or external keyboard, head mouse, gesture recognition, facial recognition, movement tracker, eye movement tracker, smart buttons, trackball, track pen, pen tablet, pen, stylus, and hand mouse. The input may include a user applying touch, voice, click, tap, type, gestures, movement (e.g., moving an eye, arm, body), and other actions.

A measurement control element 114 may be displayed on the same GUI 106 as the questionnaire 108 in an acquisition portion of the GUI, or on a separate GUI, to enable the patient to direct acquisition of body measurement data. In some implementations, user interaction with the measurement control element 114 may control activation of a capture device 116, e.g., camera, lidar scanner, etc., on the client computing device 102 (e.g., backside of a camera) to capture images, such as photos, videos, and/or LiDAR images (point clouds) of the body of the patient. In some implementations, patient interaction with the measurement control element 114 may initiate a timer delay to allow the patient 104 to get into position prior to the capture device 116 capturing images. In some implementations, captured multimedia may be analyzed to extract relevant data from the images, such as using image recognition algorithms, LiDAR software, and other data extraction algorithms that may be part of the client fitting application or a dedicated data acquisition application on the client computing device. For example, LiDAR images may be fed to a body measurement application to determine different body measurements, for example, as described below with regards to FIG. 2. In some implementations, the images may be analyzed by image recognition algorithms to extract particular body measurement data, body shape, and other visual cues regarding the patient.

In some implementations, patient medical information may be access from a patient medical information source 150, e.g., medical database, by the client computing device 102 and/or remote computing device 130. Patient medical information 152 stored in the medical information source 150 may include information regarding the medical condition being monitored and/or treated by the medical device. In some implementations, the medical condition may be relate to the fit of the wearable article, such as skin allergies, rather than or in addition to conditions being monitored or treated by the medical device. The patient medical information may be combined with the patient specific data acquired by the client computing device 102 to be inputted into the AI models.

The patient specific data (PSD) may be stored at the client computing device 102 in a PSD storage (not shown). In some implementations, the client computing device 102 may interact with the remote computing device 130 in various ways. In some implementations, the client computing device 102 may transfer patient specific data across network 122 to the remote computing device 130.

In other implementations, the client computing device 102 may include one or more AI models 136 (shown in FIG. 1 in the remote computing device 130). In some implementations, the fitting AI model may be trained and periodically retrained remotely and installed on the client computing device 102 to be used locally. At times, the updates may be pushed to the client computing device 102, for example in response to client computing device requests, on a defined schedule and/or as determined by the remote computing device.

In some implementations, the client computing device 102 may perform the selection of class of wearable article locally without communication with the remote computing device 130, for example, if the client computing device 102 does not have internet connection to network 122, on either a temporary or permanent basis. When the selection of class of wearable article is performed locally on the client computing device, a relatively smaller patient data set may be used as input, such as patient height, weight, or gender only. Due to a relatively lower computing power available locally on the client computing device, the SFA can be small and self-contained.

The remote computing device 130 may have one or more patient data storage 138 in a memory 132. The patient data storage 138 may include a fitting and demographic database (FDD) (also referred to as global patient data) in memory 132 of the remote computing device 130. In some implementations, the FDD may be an external database that is accessed by the one or more remote computing devices via the network.

The remote computing device 130 includes processor 140 that accesses the fitting assistant 134 stored in the memory 132 and may perform one or more of the described steps to select a class of wearable articles and/or predict adverse fit potential. The patient specific data may be inputted into at least one AI model 136 of the fitting assistant 134.

In some implementations, a fitting AI model may receive patent specific data to determine a class of wearable article that is predicted to provide a target fit for the patient. The fitting AI model has been trained with fitting data from previous patients. The fitting data may also be stored in the patient data storage 138 of the remote computing device 130, or may be stored in a remote storage database. Fitting data may include patient specific data of prior patients and associated wearable article class selection (either manual selection or automatic selection via the matching process). In some implementations, the prior patient may include a current patient 104 that is being fitted, where a prior selection of a wearable article class was made for the current patient 104 and rejected as inadequate for the current patient.

The fitting AI model compares the patient specific data with successful fittings of previous patients represented in fitting data designated through training of the AI model. The previous patients may have the same or similar medical conditions. The fitting data indicates that target fits were achieved to generate an output result indicating an appropriate class of wearable article for the current patient 104. In some implementations, fitting data may also include negative result data in which a class of wearable article failed to achieve a target fit for a previous patient.

In some implementations, an adverse fit potential AI model may receive patent specific data to determine adverse fit potential of a class of a wearable article for the current patient 104. The adverse fit potential AI model is trained with patient experience data from previous patients wearing particular classes of wearable articles. In some implementations, an output result of the adverse fit potential AI model that meets a trigger threshold for an actionable adverse potential, triggers the matching system to generate an alert. The alert may be transmitted across network 122 to a responsible party, such as the current patient 104, a caretaker of the patient, a medical provider, and/or representative responsible for fitting the wearable article. In some implementations, an actionable adverse potential may be used during the selection process for the wearable article as a factor to be considered by the fitting AI model in determining an appropriate class of wearable article.

The network 122 may include one or more WANs (Wide-Area Networks) and/or LANs (Local-Area Networks), which may be wired and/or wireless. In some examples, the network 122 may include the Internet and/or one or more cellular networks, among other networks. For example, the network 122 may provide a connection, for example, through a local network to a host computer or to data equipment operated by an Internet Service Provider (ISP). The ISP in turn provides data communication services through the world wide packet data communication network (the "Internet").

The network 122 may operate according to one or more communication protocols, such as Bluetooth™, LTE (Long-Term Evolution), CDMA (Code Division Multiple Access), WiMax (Worldwide Interoperability for Microwave Access), WiFi (Wireless Fidelity), WiFi Direct (Wireless Fidelity Direct), EDGE (Enhanced Data rates for GSM (Global System Mobile) Evolution), 3G (Third Generation), 4G (Fourth Generation), HTTP (Hyper-Text Transfer Protocol), TCP (Transmission Control Protocol), SIP (Session Initiation Protocol), device contact based transfer protocols, device movement based pairing protocols, and other communication protocols.

Although the network 122 is shown as a single networks, it should be understood that the network 122 may include multiple, distinct networks that are themselves communicatively linked. The network 122 could take other forms as well.

The depictions in FIG. 1 is not to be construed as limiting components of the medical wearable matching system 100 and how the matching system 100 is implemented. The matching system 100 can be implemented in different ways with additional or less devices. For example, in some implementations, the mobile device 110 may include be configured to use the fitting AI model and/or adverse potential AI model to select the wearable article and/or evaluate the fit, without communication with the remote computing device 130.

Figure 2:
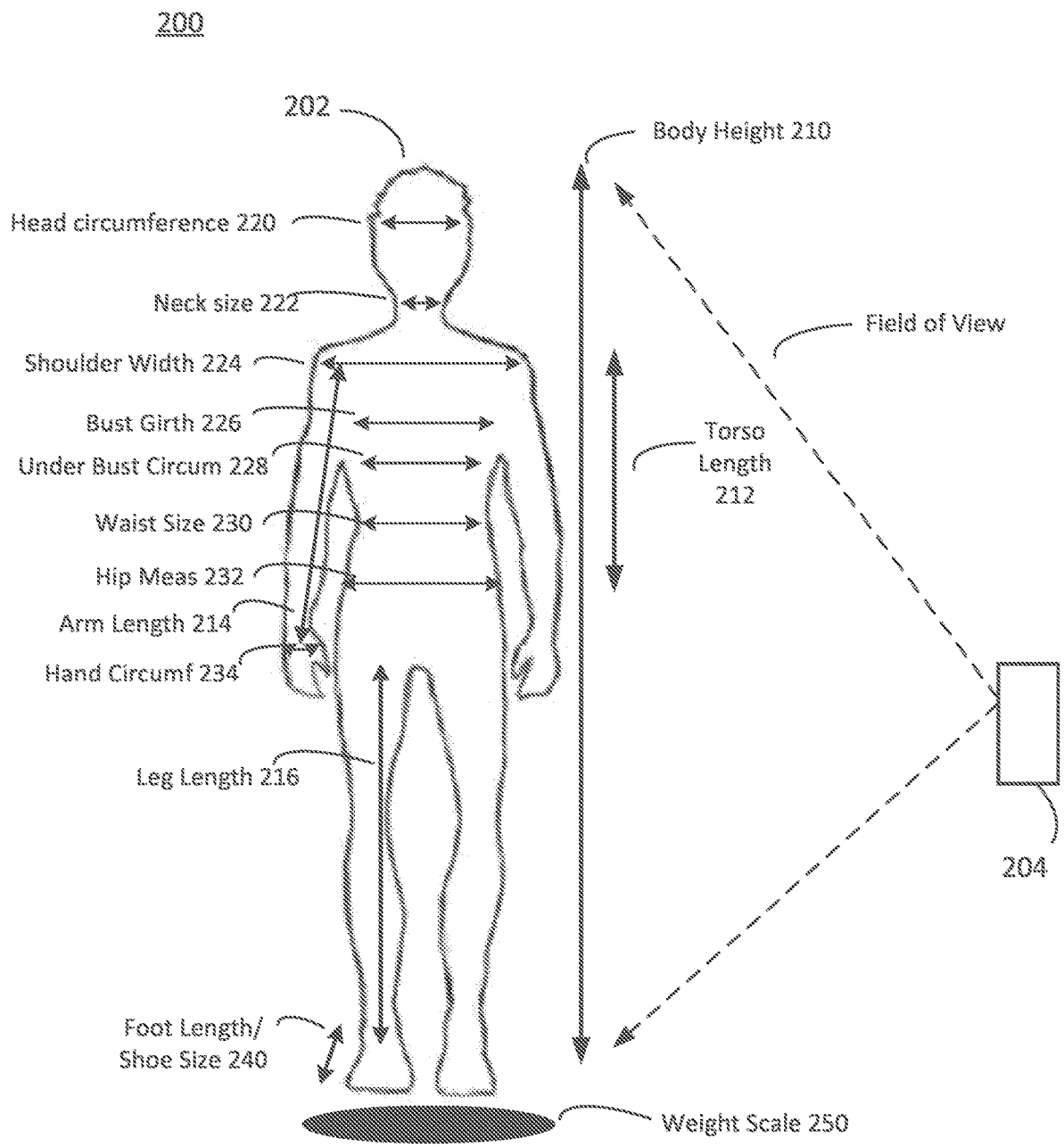
FIG. 2 is a schematic diagram of example of acquiring certain patient specific data, in accordance with some implementations.

FIG. 2 shows an example of patient specific data 200, such as patient body measurements and/or body images of a patient 202 acquired by a client computing device 204.

The body of the patient 202 or part of the patient body for measuring may be positioned within a field of view of the client computing device 204. For illustration purposes, the patient 202 is depicted in FIG. 2 as side view to the client computing device 204. It is understood that the patient may be rotated any of 360 degrees relative to the client computing device for capture and/or measurement of a particular body part. In some implementations, only a particular body part of the patient 202 may be in the field of view of the client computing device 204.

Body measurements 200 may include vertical measurements, such as body height 210, torso length 212, arm length 214, leg length 216, or other vertical length measurement. Body measurements 200 can also include horizontal measurements and/or circumference measurements, such as head circumference 220, neck size 222, shoulder width 224, bust girth 226, underbust circumference 228 (and/or over bust circumference), waist size 230, hip measurement 232, hand circumference 234, and other horizontal/circumference measurements. Body measurements 200 can also include depth measurements, such as foot length or shoe size 240.

In some implementations, body measurements 200 may also include a weight of the body. The patient 202 may stand on a weight scale 250 to obtain a weight measurement. In other implementations, weight may be determined by the client computing device by extracting information from images and other measurements captured from the patient. For example, image based weight analysis algorithms may be employed to determine weight of the patient from 2D or 3D images captured of the patient.

Other body measurements of other body parts are possible, such as eyeglass size, hat size, finger circumference, etc. Supplemental body measurements may also be detected or determined, such as percentage body fat, body mass index (BMI), etc. Any measurement or sizing conventions may be employed for body measurement data.

In some implementations, other capture devices, such as a dedicated camera, may be employed instead of or in addition to the client computing device 204 for capturing images of the body or body part or for detecting body measurements. For example, in some implementations, a capture device may take images of the body and transfer the images to the client computing device for analysis and extraction of body measurements from the images.

The particular body measurements obtained and used may be specific for the body part(s) to be worn by the wearable article and treatment contact points on the body, in which sensors and/or treatment providing components of the wearable article needs to make contact with the body to be effective. For example, in some implementations a vest-type wearable article for cardiac medical conditions may be employed on a torso of the patient with electrodes spaced proximal to the heart. In such torso-wearing articles, patient body measurement data may include a bust measurement (bust girth), underbust measurement, waist size, torso length, and/or patient height.

Target fit may be defined in quantitative or qualitative terms to signify conformity of various fit factors of the wearable article, to operations parameters needed for proper performance of the medical device as it is intended to be used. For example, operations parameters may include application of a sufficient amount of a substance, e.g. electrode gel or conductive solution, on a particular body part, proper communication between electrodes, etc. Fit factors may include wearable component-to-body contact such that a wearable component, e.g., a sensor and/or electrode, which provides monitoring or treatment is in a proper position. Other wearable components needing proper placement may include a display screen, user controls, wire leads, etc. Fit factors for component-to-body position may include body contact type factors, such as an amount of body surface area in contact by the wearable component, pressure applied to the component against body, the component positioned within target region of the body. Other fit factors may include how the wearable article falls on the body, such as, gaping of the wearable fabric relative to the body, tightness on body, fabric wrinkling or bunching, restricting of body movement, etc. Still other fit factors may relate to environmental interference of the sensor e.g., ECG electrode, to properly detect, such as reduction of noise interference by a properly fitted wearable article. In some implementations, the target fit may include an acceptable range of independent fit factors or combination of fit factors. Target fit may include weights for particular body measurements and/or other factors as more or less important to achieving the target fit.

In some implementations, a target fit may include a range of one or more body measurements that correspond with a particular class of wearable article. An example sizing chart may employ a range of underbust circumference measurements to indicate a particular class of wearable article:

Classes 1A, 1B: 28"-32"
Classes 2A, 2B: 31.5"-35.5"
Classes 3A, 3B: 35-39"
Classes 4A, 4B: 38.5-42.5"
Classes 5A, 5B: 42"-46"
Classes 6A, 6B: 45.5"-49"
Classes 7A, 7B: 48.5"-52"

The above example sizing applies to two different styles, where a first classes A is for a first style of wearable article and a second classes B is for a second style. The example chart applies to fourteen (14) different classes (1A, 1B, 2A, 2B, 3A, 3B, 4A, 4B, 5A, 5B, 6A, 6B, 7A, and 7B) of wearable article from which the matching system selects for a given patient.

In some cases, if the body measurement falls between two sizes, as a default, a lower or higher sized wearable article may be selected. In such cases, an alert may be provided to the patient, medical provider, caretaker or other relevant party, of adverse fit potential.

In still some cases, a body measurement that falls above or below a threshold may not fit within any available class of wearable article. To illustrate in the example sizing chart shown, an underbust measurement that falls less than 28 inches or greater than 52 inches may indicate that a class of wearable article may not be available for the patient. In such circumstances, a custom made or adjusted wearable article may be employed. A decision may also be made by the matching system as to whether a poor fit wearable article would be employed despite inability to achieve a target fit, e.g., the smallest class or largest class wearable article. When a poor fit wearable article is selected, an alert may be provided to the patient, medical provider, caretaker or other relevant party, of adverse fit potential.

Figure 3:
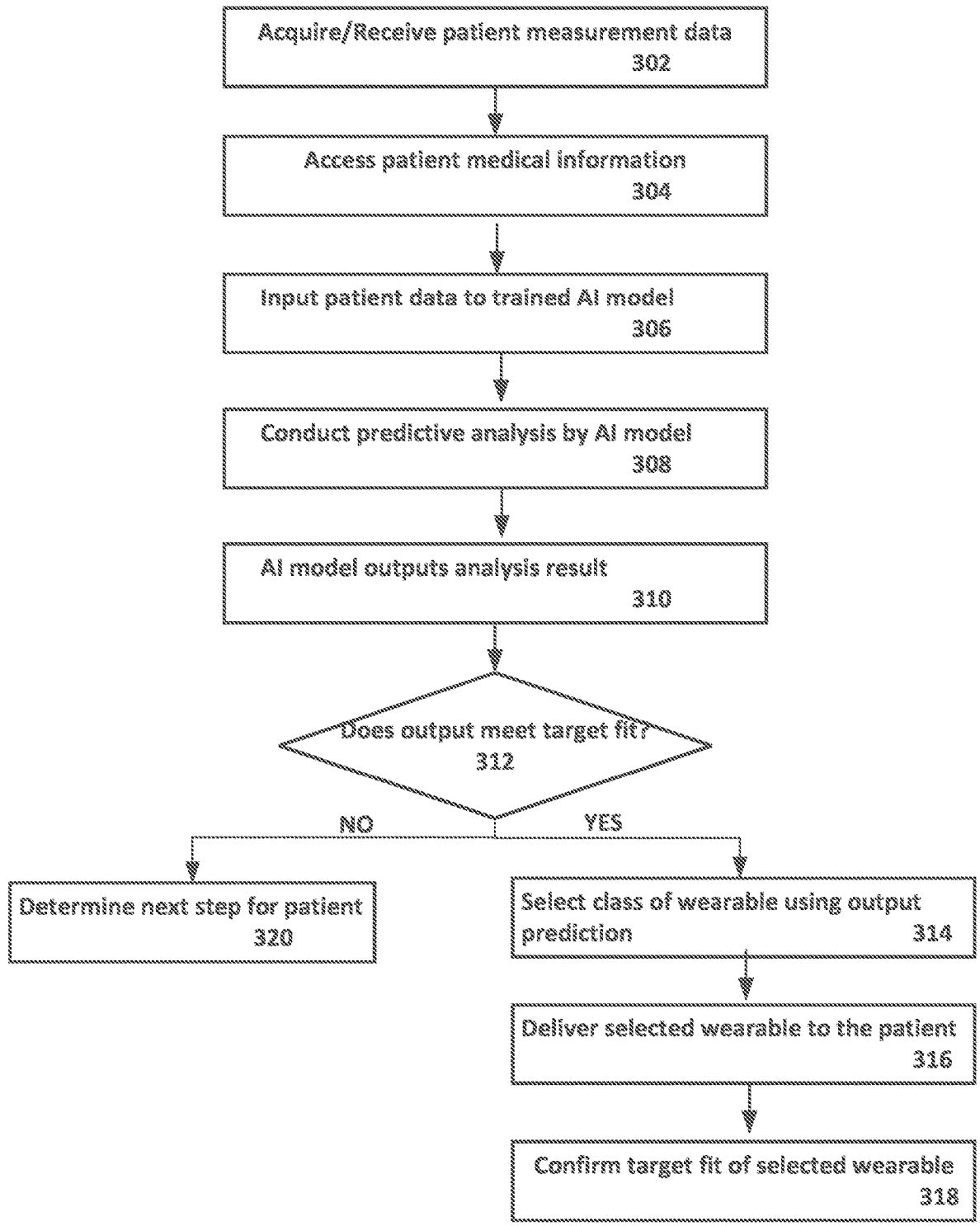
FIG. 3 is a flowchart of an example method for selecting a wearable medical article, in accordance with some implementations.

FIG. 3 shows a flowchart of an example matching process 300 to select the class of wearable article for a medical device using a fitting AI model. In some implementations, the matching process can be implemented on a mobile device application, e.g., client computing device, and/or an application running on a dedicated server, e.g., remote computing device, and/or an application hosted in the cloud. In implementations, the device or devices implementing the matching process can be stand-alone or a combination of mobile processing and cloud processing.

The steps of the wearable matching process may be performed by components of the medical wearable matching system, for example remote computing device 130 and/or client computing device 102 with reference to FIG. 1, or as a service of a cloud server. In some implementations, a remote computing device performs the selection of a class of wearable article by receiving patient specific data, for example at least a portion of patient specific data provided from the client computing device. In some implementations, the selection is performed locally by the client computing device in communication with a remote computing device, for example to receive a trained or retrained fitting AI model. In still some implementations, the selection process is performed entirely locally by the client computing device without communication with the remote computing device. In the latter implementations, limited data may be employed to train an AI model without fit data from other previous patients.

In block 302, patient measurement data is acquired (for example as described above with regard to FIG. 2) or otherwise received from a separate device or from data storage within the computing device. In block 304, patient medical information is accessed from a storage area that may be at a remote location or stored within the computing device.

The patient measurement data and patient medical information, as well as optionally other relevant patient information, are combined as patient specific data. In block 306, the patient specific data is inputted into a fitting AI model. In block 308, the fitting AI model conducts analysis on the patient specific data based on training of the fitting AI model with fitting data of previous patients. An example training and retraining process is described below with regards to FIG. 5.

The AI model may use various algorithms for the predictive analysis. For example classification analysis may be employed, for example, organizing various patient data into the categories consistent with the classes of wearable articles. The classification technique predicts a particular class value based on prior inputs, in this case including patient data (patient characteristics) and actual wearable article selection results. Other algorithms may include regression analysis, for example, machine learning involving predicting a particular value based on a set of prior data e.g., using various patient data and classes of wearable articles as dependent or independent variables. The patient data may be also organized into decision trees that are traversed by the AI model. Other algorithms may include support vector machines (SVM), naïve bayes, linear regression, logistic regression, etc.

In some implementations various portions of the patient specific data may be assigned predefined weights in which some portions are weighted more than other portions. The AI model may also factor in special circumstances of a patient that may not be present in the training dataset of fitting data from previous patients.

In block 310 the fitting AI model outputs a result of the analysis. The output result may indicate a class of wearable article that is predicted to meet a target fit. In some circumstances, none of the classes of wearable articles to choose from have the predicted potential to meet the target fit. In decision block 312 it is determined whether the output result indicates that a class of article may potentially meet the target fit.

If the output result indicates a class that meets the target fit, in block 314, a class of wearable article may be selected. In some implementations, the class indicated by the output result is selected without any additional decision making processes. In other implementations, the output result is one criteria used in a selection process, along with other criteria including special requirements of users, e.g., the patient, representative of the wearable article and/or healthcare provider, which may not have been considered or given sufficient weight by the fitting AI model.

In some implementations, the output result of the fitting AI model is a prediction of a size (e.g., extra small, small, medium, large, extra-large) of wearable article that is predicted to meet a target fit. A style is chosen, for example, by preference input information from the patient. The combination of the chosen style and predicted size is used to select a class of wearable article for the patient, e.g., class A wearable article characterized by small size and style 1.

In some implementations, the output result may be overridden by users. In case of an override of the class indicated by the output result, an alert may be generated of an adverse fit potential. Furthermore, where an override selection of the wearable article is made that is different from the output result of the fitting AI model, the override selection may be fed back to the fitting AI model for retraining.

In block 316, the wearable article is provided to the patient, for example via shipping or in-person appointment with the wearable article representative. The patient may receive training on use of the wearable article and medical device.

In some implementations, confirmation of a conforming target fit or information of non-conforming fit by the selected wearable article may be received from users, e.g., the patient, patient caretaker, representative of the wearable article, and/or healthcare provider. For example, the user may complete survey questions that provide information on whether the wearable article met the target fit or whether the target fit was accurately defined. Returns, replacement, or damage to the wearable article by the patient may provide further confirmation or non-confirming information. Such feedback information may be fed back as additional training data for the fitting AI model, as described below with regards to FIG. 5.

If the output result indicates that no class of article has potential to meet the target fit, the matching system may decide on a next course of action for the patient in block 320, according to a secondary action algorithm. For example, it may be decided that a class of wearable article may be selected as a next best option, and an alert may be provided that there may be adverse fit potential. In this case, the process proceeds to block 314 for class selection and the following steps continue accordingly.

In some cases, for example if a risk of poor operation of a wearable medical article is too great considering the medical condition of the patient, the process may indicate a selection process failure and no wearable article is selected. In still some implementations, information may be provided that alteration or customization of a class of wearable article may be necessary to increase target fit potential.

Some or all of the matching process 300, or any other processes described herein, or variations and/or combinations of those processes, may be performed under the control of one or more computer systems configured with executable instructions and/or other data, and may be implemented as executable instructions executing collectively on one or more processors. For example, the matching process 300 may be adapted to include steps for treating a patient, such as a defibrillator shock based on the determined episodes.

In some implementations, matching process 300 may include additional steps, such as remote education or advising of the patient on proper wear and maintenance of the wearable article.

Figure 4:
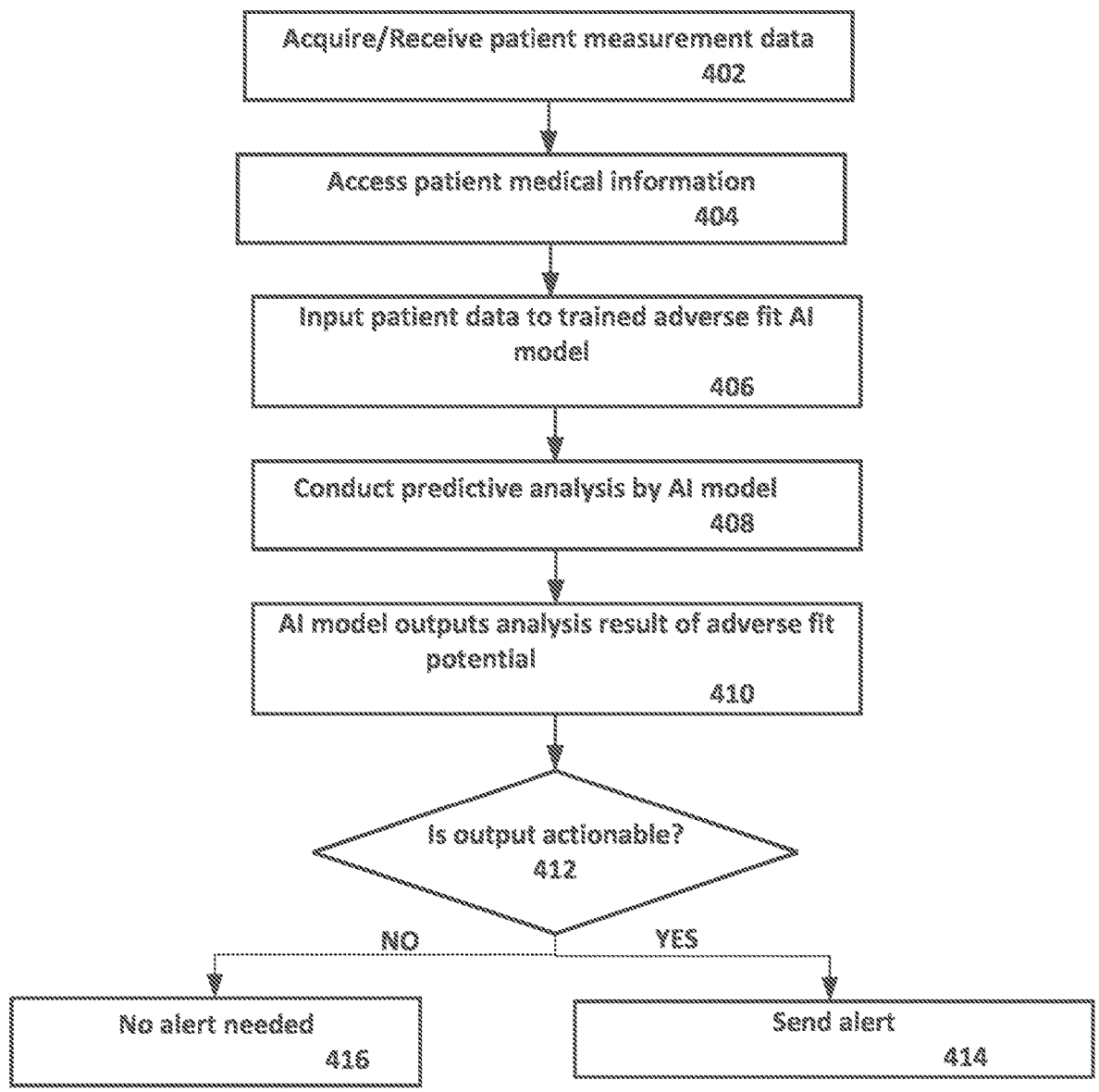
FIG. 4 is a flowchart of an example method for determining potential operational issues regarding the fit of a wearable medical device on a patient, in accordance with some implementations.

FIG. 4 shows an example pre-assessment process 400 for determining potential operational issues of the medical device regarding the fit of a wearable medical device on the patient. Often the pre-assessment process 400 may be performed after selection of a class of wearable article for a patient and prior to the patient beginning to wear the wearable article. In some implementations however, the pre-assessment process 400 may be used as a criteria to feed back into the selection process to accept or reject an initial selection of a wearable article made by the matching system. In still other implementations, the pre-assessment process 400 may be used if the patient data is outside of criteria for any class of wearable article, e.g., the patient is too large or small, and a target fit may not be achieved. In these situations, a next best selection may be made using the findings of the pre-assessment process 400.

The pre-assessment may also take place as the patient wears the wearable article. For example, should patient data change, such as patient measurements, after starting to wear the wearable article, the pre-assessment process 400 may be activated to determine if the change in patient data may adversely affect the fit and performance of the medical device.

In some implementations, the adverse fit potential process 400 may be conducted in conjunction with the matching process described with regards to FIG. 3 above. For example, one AI model may analyze patient specific data for fit potential and another AI model may analyze the patient specific data for adverse fit potential. The selected class of wearable article and any adverse fit potential alert may be both transmitted to a user. In other implementations, adverse fit potential may be conducted independent of the matching process, e.g., at a subsequent time from the matching process or for patients using a wearable article that was not selected by the matching process described herein.

The steps of the wearable matching process are performed by components of the medical wearable matching system, for example remote computing device 130 and/or client computing device 102 with reference to FIG. 1. In some implementations, a remote computing device (which can include a cloud service) performs the adverse fit potential analysis by receiving patient specific data from the client computing device. In some implementations, the adverse analysis is performed locally by the client computing device in communication with a remote computing device, for example to receive a trained or retrained adverse fit potential AI model. In still some implementations, the adverse analysis process is performed entirely locally by the client computing device without communication with the remote computing device. In the latter implementations, limited data may be employed to train an AI model without patient experience data from other previous patients.

In block 402 patient measurement data is acquired or otherwise received and in block 404, patient medical information is accessed from a storage area. The patient measurement data and patient medical information, as well as optionally other relevant patient information, are combined as patient specific data and in block 406 inputted into an adverse fit potential AI model.

In block 408, the adverse fit potential AI model conducts adverse analysis on the patient specific data based on training of the adverse fit potential AI model with patient experience data of previous patients. An example training and retraining process of the adverse fit potential AI model is described below with regards to FIG. 5.

The adverse analysis predicts potential patient fit issues that could have adverse effects on the performance and efficacy of the wearable device. For example, excessive ECG noise by ill positioned sensors of a wearable article may affect algorithm performance in analyzing ECG data and determining if a cardiac event is occurring.

Such adverse fit potential results are outputted by the AI model in block 410. The output results are assessed in decision block 412 to determine if there is an adverse fit potential and if a potentially adverse effect reaches a threshold to be actionable. If such an adverse fit potential is found to be actionable, in block 414, an alert may be provided to one or more user devices, such as the client computing device, patient caretaker device, healthcare provider computing system, and/or wearable article representative device. Where no adverse fit potential is found or if an adverse fit potential fails to meet an actionable threshold, no alert may be provided. A record of the adverse fit potential analysis may be stored. A user may be notified that the analysis is complete and did not find a finding of an actionable adverse fit potential.

Some or all of the adverse fit potential process 400, or any other processes described herein, or variations and/or combinations of those processes, may be performed under the control of one or more computer systems configured with executable instructions and/or other data, and may be implemented as executable instructions executing collectively on one or more processors. In some implementations, matching adverse fit potential process 400 may include additional steps.

Figure 5:
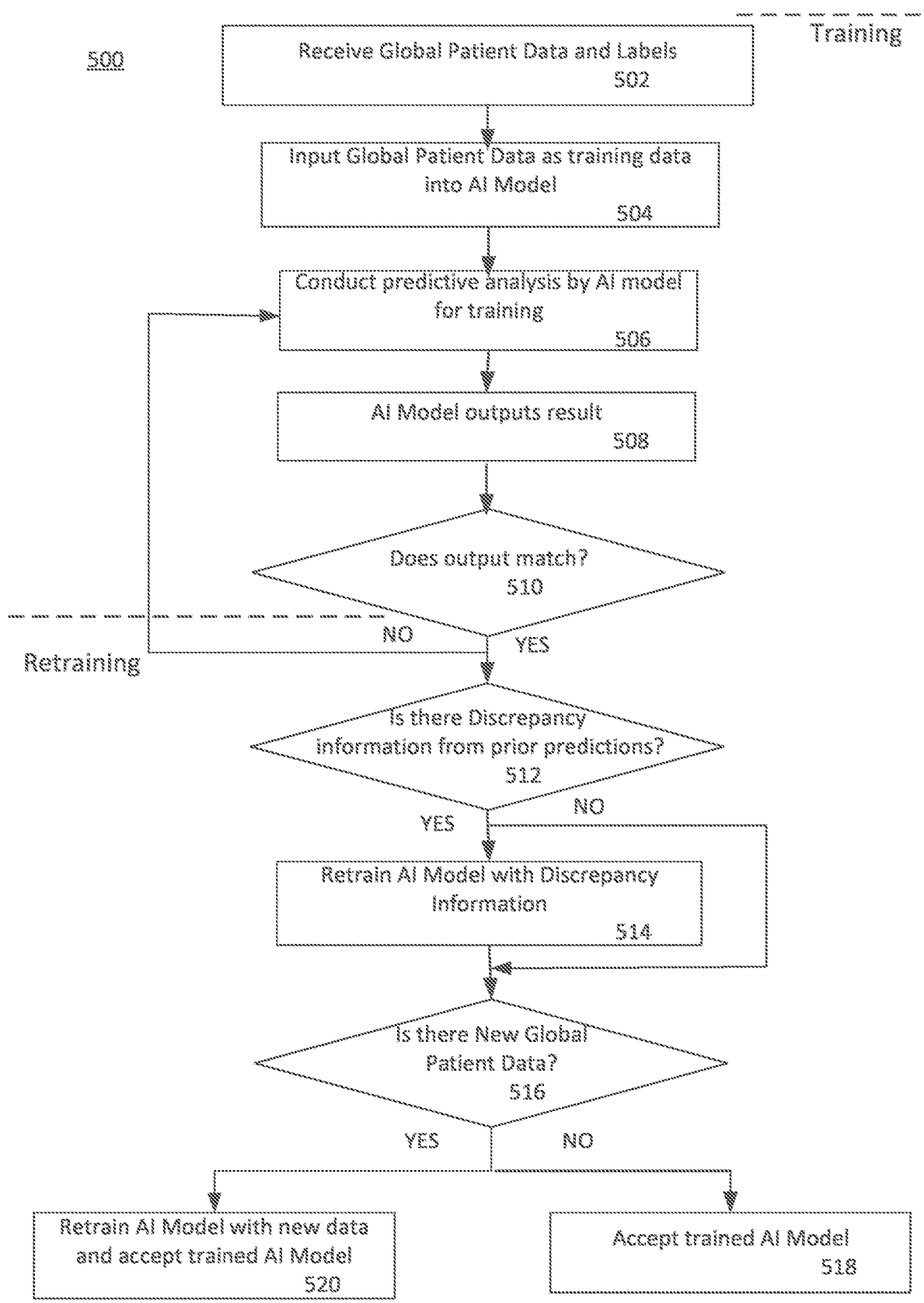
FIG. 5 is a flowchart of an example method for training and retraining an AI model for use in the medical wearable matching system, in accordance with some implementations.

FIG. 5 shows a flowchart of an example method to train and retraining the fitting AI model and/or adverse fit potential AI model. In some implementations, the techniques to train the machine learning model may employ supervised classification algorithms, such as logistic regression algorithms. In some implementations, unsupervised or semi-supervised techniques may be employed.

In block 502, global patient data of previous patient is received or otherwise accessed, such as access to the FDD shown in FIG. 1. For an AI model, the global patient data includes fitting data of previous patients. In some implementations, the global patient data may be processed to generate training data for the fitting AI model. The fitting data processed for training includes patient measurement data correlated with patient medical condition data and/or other patient data. The fitting data may be associated with labels of a class of wearable that the patient had used and to which the dataset relates. The labels may also include information describing whether the class of wearable article was a successful fit or unsuccessful fit. The AI model is preloaded with a target fit for the training datasets. For an adverse fit potential AI model, the training data may include fitting data and also include additional patient experience data and labels as to whether a dataset is associate with a found adverse effect experience by a patient and/or medical device. Once processed, in block 504, the training data may be inputted into the AI model for training.

In block 506, the AI model conducts predictive analysis on the training data. The training of the AI model may include determining patterns in the previous patient data that leads to successful fitting with a particular class of wearable. Based on the analysis, the AI model outputs a result of the analysis, in block 508. Where a fit prediction model is being trained, the output may include labels on the class of wearable article that the AI model predicts would be suitable to lead to a target fit for a particular training dataset.

In decision block 510, the output result is compared with the training dataset inputted into the AI model to determine whether the output result matches with the associate labels. For a fitting AI model, the output result may be labels of classes of wearable that are predicted to achieve the target fit for associated datasets. For an adverse fit potential AI model, the output result may be labels of whether particular classes of wearable article associated with datasets are predicted to have associated adverse effects on the operation of the medical device or other adverse effects related to the patient.

If it is decided in decision block 510 that the output results match the training datasets, the process continues. If there is a finding that the output results fail to match, the AI model is retrained by returning to block 506 and conducting predictive analysis again until the output result matches the training dataset. If a match is not achieved after a threshold number of tries, the analysis algorithm and/or training dataset may be assessed to find a solution to the failures.

In decision block 512, it is determined whether there is discrepancy information from prior AI model output results, in which the output failed to result in a target fit for a patient or dissatisfaction is expressed by the patient or other user associated with the patient. Discrepancy information may include patient survey information, return data, replacement data, and/or wearable article damage, for previous wearable articles predicted by the fitting AI model or manual selection to provide target fit for previous patients. For example, for the fitting AI model, if a selected class of wearable article is tried on by the patient and found to not achieve a target fit, the discrepancy information may be fed back into the AI model for retraining in block 514. For example for the adverse fit potential AI model, if a selected class of wearable article results in an adverse effect not detected by the AI model after prediction analysis, the discrepancy information may be used for retraining in block 514. After discrepancy information retraining is complete, the process proceeds to decision block 516 described below.

If no discrepancy information is received, the process skips the discrepancy information retraining and continues to decision block 516 to determine if new additional fitting data is available. As the AI models are used for new patients, the pool of fitting data and patient experience data grows. The new fitting data is used for retraining in block 520 to increase accuracy of the AI models. Where no new training data is available, in block 518, the AI model is accepted as being trained for use.

Some or all of the training/retraining process 500, or any other processes described herein, or variations and/or combinations of those processes, may be performed under the control of one or more computer systems configured with executable instructions and/or other data, and may be implemented as executable instructions executing collectively on one or more processors. In some implementations, training/retraining process 400 may include additional steps.

Figure 6A:
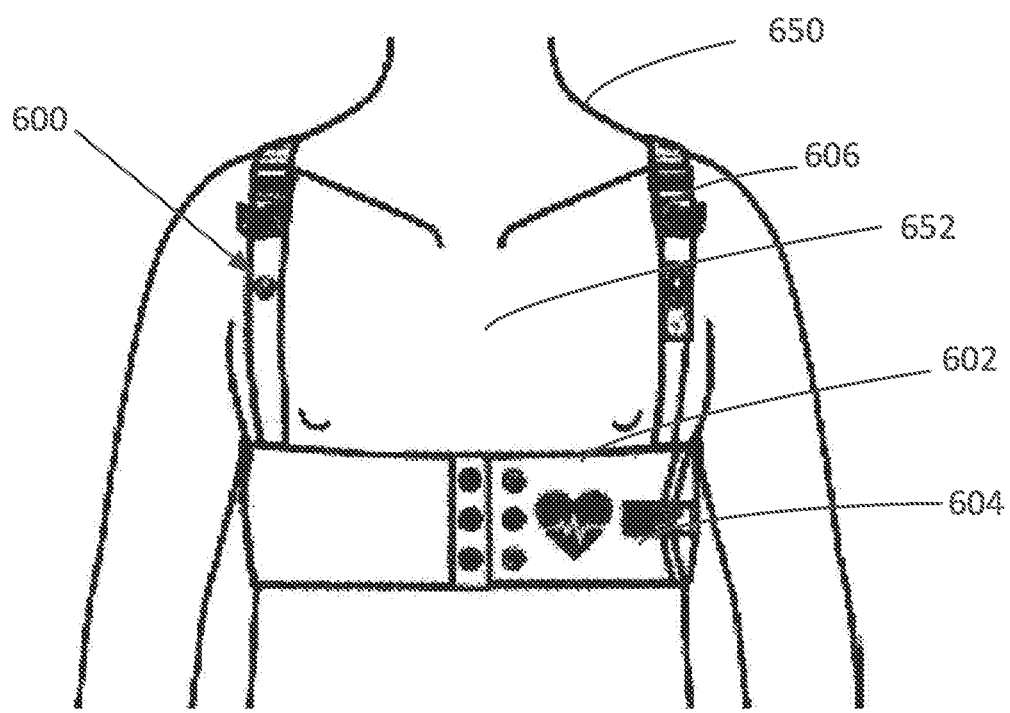
Figure 6B:
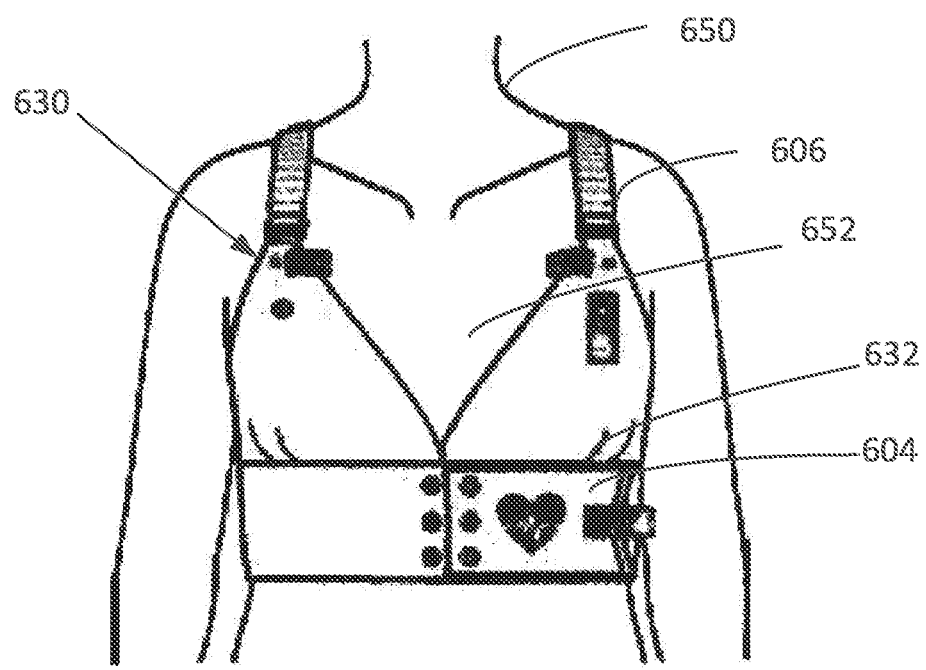

As shown variously in FIGS. 6A and 6B show different classes of vest-type styles of wearable articles. FIG. 6A illustrates a first style wearable article 600 having a support structure 602 with an underbust fit. FIG. 6B illustrates a second style wearable article 630 having a support structure 632 with a bust cover fit.

The vest garment style wearable article may include a fabric material base, which may house a variety of components for the medical device. The support structure 602, 632 has a main body portion 604 fitted around a torso 652 of the patient 650 and two shoulder straps 606 with one shoulder strap designed to fit over each shoulder of the patient 650 from the front side of the patient to the back side of the patient. The shoulder straps 606 may be adjustable to accommodate a range of torso lengths. The support structure may also be implemented with a single shoulder strap, for example, that may wrap around the neck, or around one shoulder at an angle, or as a full vest rather than having shoulder straps. The main body portion 604 may be installed to fit snug around the torso with the shoulder straps 606 holding the main body portion 604 in place onto the torso 652 of the patient 650. In this manner, the support structure 602 may encircle the patient 650 without a need for adhesives to attach the support structure onto the patient. The main body portion 604 may be enclosed around the torso with fasteners, such as snaps, buttons, hook and loop, clasps, clamps, buckles, catchers, ties, etc., or with flexible fabric or elastic to allow stretch for slippage onto the torso. Other enclosures are possible.

The underbust style wearable article (Style 1) 600 may use long shoulder straps 606 to engage the support structure under the bust than the bust cover style wearable article (Style 2) 630. The bust cover style wearable article (Style 2) includes additional fabric to cover the bust area of the patient 650 and short shoulder straps 606 to engage the support structure above the bust area. The fitting AI model may decide on a Style 1 or Style 2 class of wearable article based on various patient specific data such as body shape, e.g., more pronounced bust girth, gender (although not necessarily dispositive to selecting a style), patient preference, patient comfort, etc.

The depictions in FIGS. 6A and 6B are not to be construed as limiting how the styles of wearable article classes or how the wearable article is implemented or worn. The support structure 602 of a torso fitted wearable article can be implemented in many different ways to engage with at least a portion of the torso of the patient. For example, it can be implemented in a single element or a combination of multiple elements, which may be coupled together. In some implementations, support structure 602 could include a vest, a half-vest, or other type of garment that engages with at least a portion of the torso. In some implementations, support structure 602 could include a harness, one or more belts or straps, etc. that fit on a torso or other accessible parts of the patient. The support structure 602 can also be worn around hips, over the shoulder, around appendages, etc. In implementations, such items can be worn similarly to analogous articles of clothing. Such items can be worn parallel to or underneath other articles of clothing.

Figure 7:
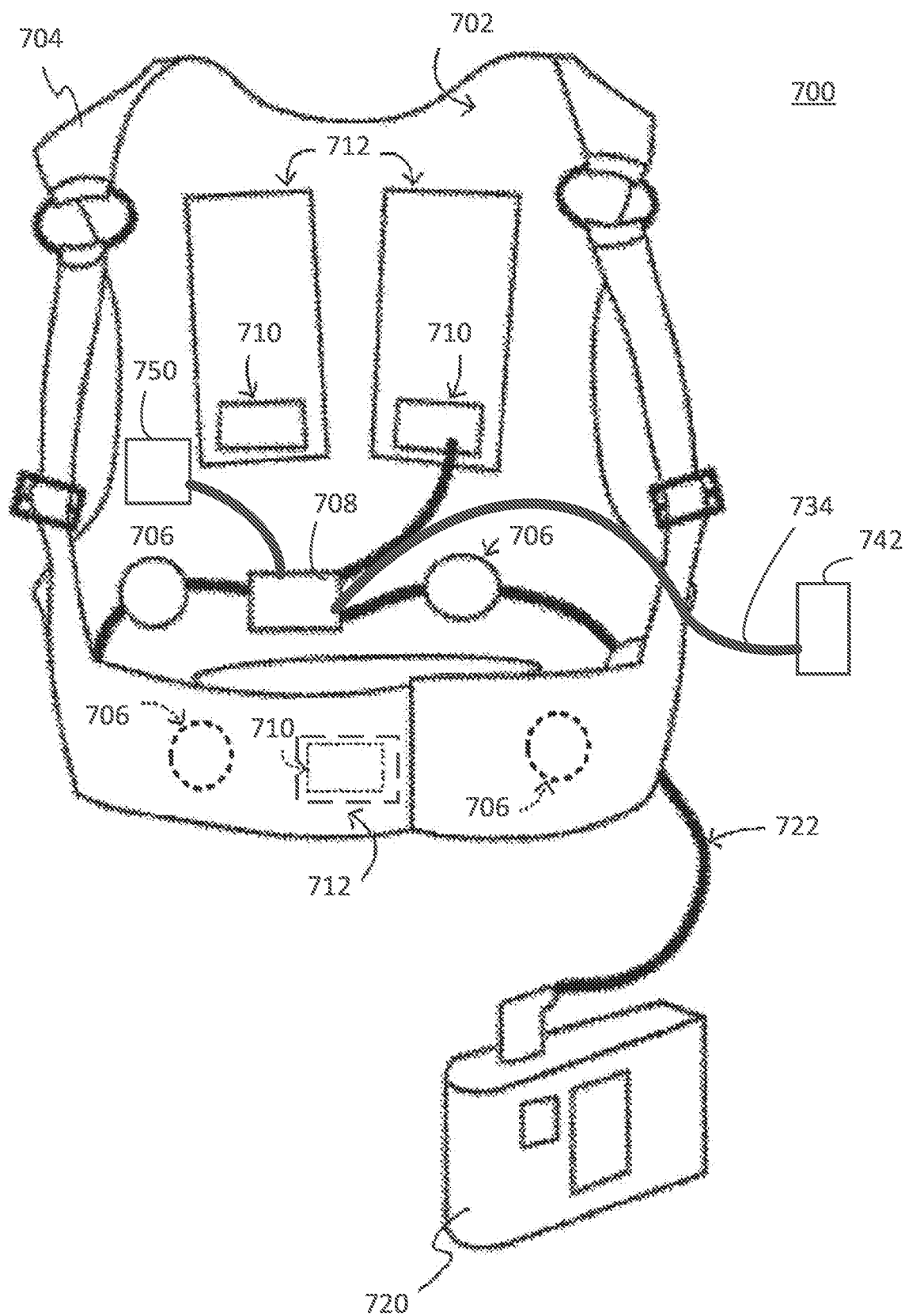
FIG. 7 is a schematic diagram of a medical device including a vest-type wearable article with components, in accordance with some implementations.

FIG. 7 shows an example of a medical device 700 having a vest type wearable article 702 configured with components for cardiac monitoring and treatment. The medical device 700 includes the wearable article 702 with a support structure 704 that houses various components such as signal source components, one or more external signal source components 742 that are not housed by the support structure 704, and an electronic main unit 720 in communication with the components of the wearable article 702. In some implementations, the main unit 720 may be carried by the patient separately from the support structure 704, such as with a purse, belt, strap over the shoulder, and so on.

Signal source components include sensors and/or transducers, to collect health signals associated with health parameters relevant assessing the patient for health events. Health parameters may include any combination of patient physiological parameters, patient state parameters, system parameters, and environmental parameters. Other types of signal source components are possible, including clocks to track time and date. Signals from the various source components feed into detectors for processing and generating of associated health data.

Components held by the support structure 704 may include one or multiple electrodes 706 attached to the wearable article by various attachment features of the wearable article, such as pockets, hook and loop, adhesives, etc. The support structure 704 may also accommodate a hub 708 to communicate with the various signal source components held by the support structure 702, as well as communicate with one or more external signal source components 742, such as an oximeter, not housed by the support structure 702. The hub 308 may further communicate with the main unit 720.

Additional internal sensors 750 that may be held by the support structure 702 may include an audio detector such as heart-sound/phonocardiogram, patient temperature thermometer, GPS, pressure sensors, optical sensors such as photoplethysmography, etc. to produce signals used in generating health data about the patient. A microphone may be positioned to detect frequency, volume, intensity, regularity, etc. of heart beat. The microphone may also detect frequency, volume, regularity, etc. of breaths. Such additional internal sensors 750 may be wired or wirelessly coupled to hub 708 to provide signals produced by the additional internal sensors 750 according to the sensors sensing of parameters of the patient.

External signal source component 742 may be attached to other parts of the patient, for example, which may be more conducive to sensing a physiological parameter rather than at the torso. Examples of other signal source components may include sensors or transducers such as a perfusion sensor, a pulse oximeter, a device for detecting blood flow (e.g. a Doppler device), a sensor for detecting blood pressure (e.g. a cuff), an optical sensor, illumination detectors and sensors working together with light sources for detecting color change in tissue, a device that can detect heart wall movement, a sound sensor, a device with a microphone, a Saturation of Peripheral Oxygen (SpO2) sensor, a GPS for example used to determine a sudden cardiac arrest or other cardiac conditions, and so on.

An example external signal source component 742 may include an oximeter (also referred to as an "SpO2 sensor") engaged with a body part, such as a finger, of the patient in which blood flow is easily detected. The oximeter may detect a reduction in blood oxygen level and signals or health data from the oximeter can be time-synchronized with other health data, such as the ECG and respiration data. Reduced blood oxygen saturation level may indicate a respiratory disturbance of the patient.

The hub 708 can receive data from the external signal source component 742 and transfers instructions or activation signals to the external signal source component 742 via wired cable connection and/or a wireless communication mechanism. In some implementations, an external signal source component 742 may transfer signals directly to main unit 720 rather than to hub 708.

Sensing electrodes 704 are removably fixed to an inside of the support structure 302 to make contact with the skin of the patient directly or through a conductive medium, such as an electrolyte. The sensing electrodes 304 may be electrically coupled to main unit 320 or to the hub 308 via electrode cable 722. The electrodes 704 may be functional as both therapy and monitoring electrodes, or just monitoring electrodes without therapy functionality. Sensing electrodes 704 may be configured to produce electrical signals for ECG data and/or respiration data, e.g., AC signals for respiratory impedance determination, or DC signals. Sensing electrodes 806 may be one or more transducers configured to acquire electrical signals indicative of heart activity, such as ECG signals and respiratory signals, e.g., impedance signals from variating AC current and DC current signals. The ECG of the patient can be sensed as a voltage difference between sensing electrodes 704.

The electrodes 704 may produce signals for ECG interpretations and for respiration assessments. Electrodes 704 may be one or more transducers configured to acquire electrical signals indicative of heart activity, such as ECG signals and respiratory signals, e.g., impedance signals from variating AC current and DC current signals. The ECG of the patient can be sensed as a voltage difference between sensing electrodes 704.

In some implementations, the medical device 700 can be configured to provide cardiac treatments directly to the patient, such as defibrillating the patient via defibrillation electrodes 710, in addition to monitoring health parameters. Defibrillation can be performed by defibrillate components of the monitoring system delivering an electrical charge to the body of the patient in the form of an electric shock. The electric shock can be delivered in one or more pulses.

Based on the findings of a cardiac event by a processor of the medical device 700, the processor may further determine that treatment is warranted. The processor may activate a discharge circuit to deliver an appropriate shock treatment to the patient. In some implementations, when the determination is to shock, an electrical charge pulse is delivered to the patient. Delivering the electrical charge is also known as discharging. Shocking can be for defibrillation, pacing, and so on.

Defibrillation electrodes 710 may be contained in pockets 712 spaced throughout the support structure 704 of the wearable article 702. Inside of pockets 712 may be made of loose netting so that the defibrillation electrodes 710 can contact the body of the patient. Contact may be further facilitated by injection of conductive fluid deployed by an injection port held by the support structure 704 proximal to the defibrillation electrodes 710.

When the defibrillation electrodes 710 make sufficient electrical contact with the body of the patient, the medical device can administer, via the defibrillation electrodes 710, a brief, strong electric pulse through the body. The pulse is also known as defibrillation pulse, shock, defibrillation shock, therapy, electrotherapy, therapy shock, etc. The pulse is intended to go through and restart the heart, in an effort to save the life of the patient. The defibrillation pulse can have an energy suitable for its purpose, such as at least 100 Joule ("J"), 200 J, 300 J, and so on.

In some implementations, cardiac treatment may include providing a pacing pulses with energies similar to pacers rather than defibrillators, if the medical device 700 determines that pacing is appropriate according to the health data acquired by the medical device 700. For pacer implementations, at least some stored electrical charge can be caused to be discharged via at least two of the defibrillation electrodes 710 through the patient, so as to deliver to the patient a pacing sequence of pacing pulses. The pacing pulses may be periodic, and thus define a pacing period and the pacing rate.

In some implementations, defibrillation electrodes 710 may be multi-functional to also provide electrical signals generate ECG data and/or respiratory data. In such implementations, the medical device 700 may include both defibrillation electrodes 710 and sensing electrodes 706 or may include the multi-functional defibrillation electrodes 710 without also dedicated sensing electrodes 706.

In some implementations, the medical device may take various forms or combination of forms. For example, the wearable article may include one or more patches, one or more bands, and/or a torso fitted garment to house various components of the medical monitoring device.

While the above-described implementations are directed to monitoring devices for cardiac monitoring and capturing ECG data, other implementations include medical devices having one or more implanted sensors for which ECG and/or other physiological waveform data is collected and can be displayed. In view of the present disclosure, the above-described implementations of a user interface for capture and display of data can be adapted for waveforms other than ECG. For example, such data can include but are not limited to: electroencephalogram (EEG), capnography, electrodermal activity (EDA), transthoracic impedance (TTI), photoplethysmography, SpO2, heart-sound/phonocardiogram, electromyography (EMG), etc. Implementations enable a user to control a user interface to capture and/or select a portion of data. The user can then, for example, use the user interface to concurrently display the baseline/comparator with other waveforms or other portions of the same waveform for comparison.

The support structure shown in FIG. 7 illustrate a vest-type garment wearable medical monitoring device. In some implementations, the medical monitoring device may take various forms or combination of forms. For example, the wearable structure may include one or more patches, one or more bands, and/or a torso fitted garment to house various components of the medical monitoring device.

Figure 8:
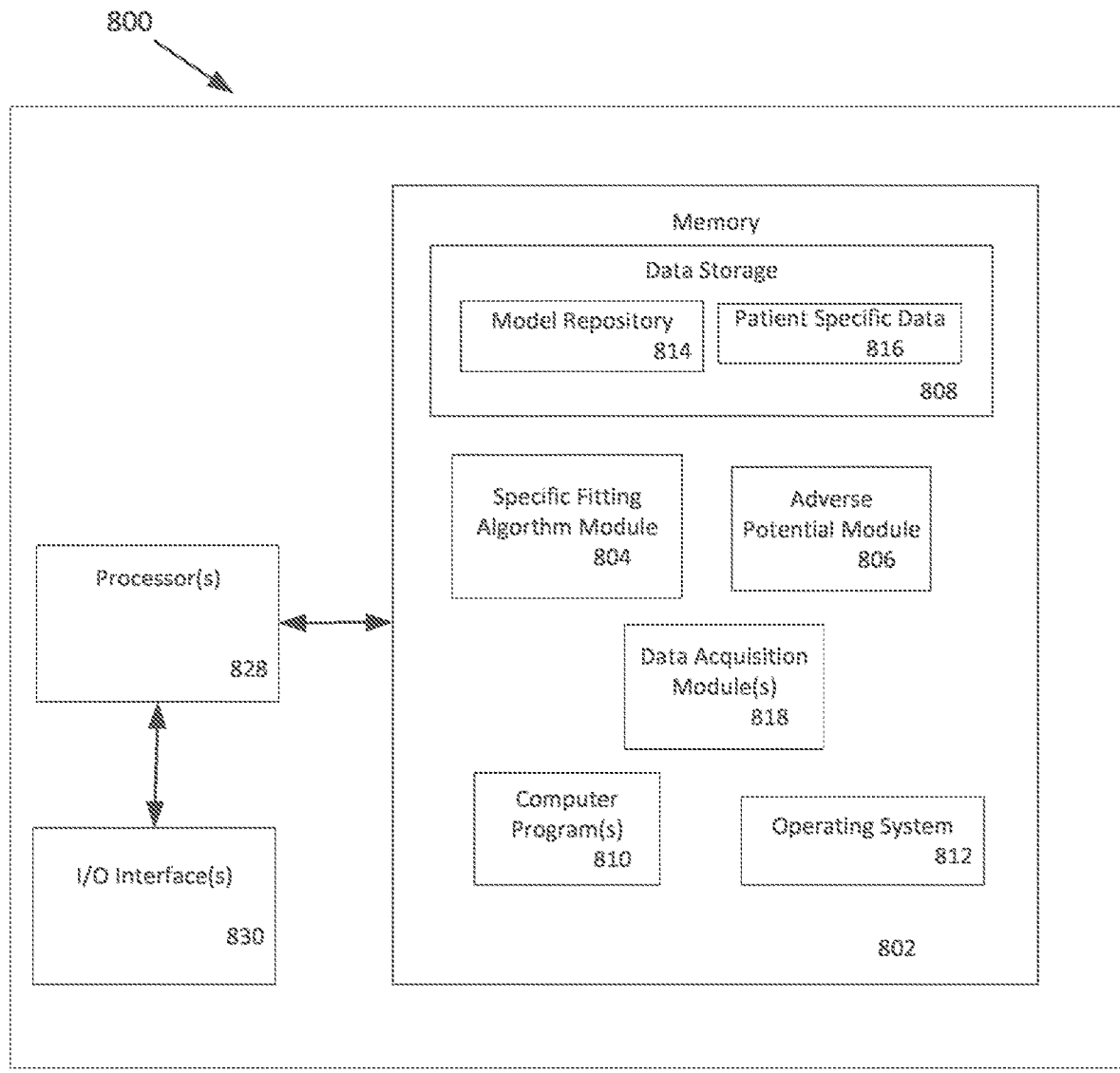
FIG. 8 is a block diagram illustrating an example local client computing device upon which wearable medical device fitting processes may be implemented, in accordance with some implementations.

FIG. 8 shows an example client computing device 800, which may implement some of the wearable article matching processes described herein. The computer device 800 may include memory 802, processor 828, and I/O interface 830. The various elements of the client computing device 800 are shown in FIG. 8 as discrete/separate elements for purposes of illustration and explanation. According to some embodiments, it is possible to combine some of these elements into a single element or device. Additional components may also be included in the computing device.

The memory 802 of the client computing device 800 is for storing information within the client computing device 800. Memory 802 may be a random access memory (RAM) or other dynamic storage device, coupled to a bus for storing information and instructions to be executed by the processor 828. The memory 802 may also be used for storing temporary variables or other intermediate information during execution of instructions to be executed by the processor 828. Such instructions, when stored in non-transitory storage media accessible to the processor 828, render the client computer system 800 into a special-purpose machine that is customized to perform the operations specified in the instructions.

The memory 802 may be any suitable data storage, memory and/or non-transitory computer-readable storage media, including electronic storage devices such as random-access memory (RAM), read-only memory (ROM), magnetic storage device (hard disk drive or the like), flash, optical storage device (CD, DVD or the like), magnetic or optical disk, or other tangible media suitable for storing instructions (e.g., program or software instructions) for execution by the processor 828. For example, a tangible medium such as a hardware storage device can be used to store the control logic, which can include executable instructions. The instructions can also be contained in, and provided as, an electronic signal, for example in the form of software as a service (SaaS) delivered from a server (e.g., a distributed system and/or a cloud computing system).

Data store 808 may store various data including patient specific data 816 (which can include LiDAR images, video, photos, spreadsheets, text files, etc.), an AI model repository 814 for storing, aggregating, updating, managing and retrieving the trained AI models applications (e.g. fitting AI model and adverse potential AI model), and other data.

At least a portion of the information may also be stored on a disk drive or other computer readable storage device (not shown) within the client computing device 800. Such storage device include a floppy disk device, a hard disk device, an optical disk device, or a tape device, digital cards, a flash memory or other similar solid state memory device, or an array of devices.

Various modules or other computer programs 810, also referred to as programs, software, software applications or code, are stored within memory 802 and contain instructions that, when executed, perform one or more methods, such as those described herein. The computer program may be tangibly embodied in an information carrier such as computer or machine readable medium, for example, the memory 802, storage device or memory on processor 828. A machine readable medium is any computer program product, apparatus or device used to provide machine instructions or data to a programmable processor.

Data acquisition module(s) 818 may be provided to facilitate capture of patient specific data. For example, data acquisition module may be initiated to control capture of patient specific data through a data measurement control element on a GUI as in 114 in FIG. 1. In some implementations, capture hardware may be controlled through data acquisition module 818. The client computing device 800 may include specialized hardware (e.g., camera(s), LiDAR components, etc.) (not shown) to capture patient measurement data. Such specialized hardware may transfer patient specific data to the client computing device 800 through I/O interface 830 (described below).

A specific fitting algorithm (SFA) module 804 may accept output results from the fitting AI model and use the output results to select a class of wearable article. The SFA may be limited in the pool of patient data that may be processed due to limited resources of the client computing device. For example, the patient data may include text data and exclude images and multimedia data. An adverse potential module 806 may accept output results from the adverse potential AI model and determine if an actionable adverse potential is detected, and if actionable, may generate an alert accordingly.

Any suitable programming languages and programming techniques may be used to implement the routines of particular embodiments. Different programming techniques may be employed such as procedural or object-oriented. The routines may execute on a single processing device or multiple processors. Although the steps, operations, or computations may be presented in a specific order, the order may be changed in different particular embodiments. In some particular embodiments, multiple steps shown as sequential in this specification may be performed at the same time. A number of implementations have been described. Features described with conditional language may describe implementations that are optional. The functional blocks, methods, devices, and systems described in the present disclosure may be integrated or divided into different combinations of systems, devices, and functional blocks as would be known to those skilled in the art.

The client computing device 800 may implement the techniques described herein using customized hard-wired logic, one or more ASICs or FPGAs, firmware and/or program logic which in combination with the computer system causes or programs the client computing device 800 to be a special-purpose machine. According to one implementation, the techniques herein are performed by the client computing device 800 in response to the processor 828 executing one or more sequences of one or more instructions contained in the memory 802. Such instructions may be read into the memory 802 from another storage medium. Execution of the sequences of instructions contained in the memory 802 causes the processor 828 to perform the process steps described herein.

In alternative implementations, one or more methods can be implemented in hardware (logic gates, etc.), or in a combination of hardware and software. Example hardware can be programmable processors (e.g. Field-Programmable Gate Array (FPGA), Complex Programmable Logic Device), general purpose processors, graphics processing units (GPUs), Application Specific Integrated Circuits (ASICs), and the like. One or more methods can be performed as part of or component of an application running on the system, or as an application or software running in conjunction with other applications and operating system 812.

The term "storage media" as used herein refers to any non-transitory media that store data and/or instructions that cause a machine to operate in a specific fashion. Such storage media may include non-volatile media and/or volatile media. Non-volatile media includes, for example, optical or magnetic disks. Volatile media includes dynamic memory, such as the memory 802. Common forms of storage media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, an EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire, and fiber optics, including the wires that include the bus. Transmission media can also take the form of acoustic or light waves, such as those generated during radio-wave and infra-red data communications.

Various forms of media may be involved in carrying one or more sequences of one or more instructions to the processor 828 for execution. For example, the instructions may initially be carried on a magnetic disk or solid state drive of a remote computer. The remote computer can load the instructions into its dynamic memory and send the instructions over a network connection. A modem or network interface local to the client computing device 800 can receive the data. The bus carries the data to the memory 802, from which the processor 828 retrieves and executes the instructions. The instructions received by the memory 802 may optionally be stored on a storage device either before or after execution by the processor 828.

Client computing device 800 further includes operating system 812. Any operating system 812, e.g., mobile operating system, that is supports the matching processes described herein performed by the client computing device 800 may be employed.

The processor 828 may process instruction for execution within the client computing device 800 including instructions stored in memory 802 or on the data store 808. The processor 828 may coordinate computing device components, e.g. applications, wireless or wired communication through interfaces, etc. In some implementations, multiple processors and buses may be used.

The processor 828 may be implemented as a chipset of chips that include separate and multiple analog digital processors. The processor may also be implemented using various architectures. For example, the processor 828 may be a CISC (Complex Instruction Set Computer) processor, RISC (Reduced Instruction Set Computer) processor or MISC (Minimal Instruction Set Computer) processor, mobile device processors, etc.

The "processor" as used herein, includes any suitable hardware and/or software system, mechanism or component that processes data, signals or other information. A processor may include a system with a general-purpose central processing unit, multiple processing units, dedicated circuitry for achieving functionality, or other systems. Processing need not be limited to a geographic location, or have temporal limitations. For example, a processor may perform its functions in "real-time," "offline," in a "batch mode," etc. Portions of processing may be performed at different times and at different locations, by different (or the same) processing systems.

The Input/Output (I/O) interface 830 can interface to other input and output devices. In some implementations, the I/O interface 830 can connect to interface devices such as input devices (keyboard, pointing device, touchscreen, microphone, camera, scanner, sensors, etc.) and/or output devices (display devices, speaker devices, printers, motors, etc.). Some implementations can provide a microphone for capturing sound (e.g., as a part of captured images, voice commands, etc.), audio speaker devices for outputting sound, or other input and output devices.

Figure 9:
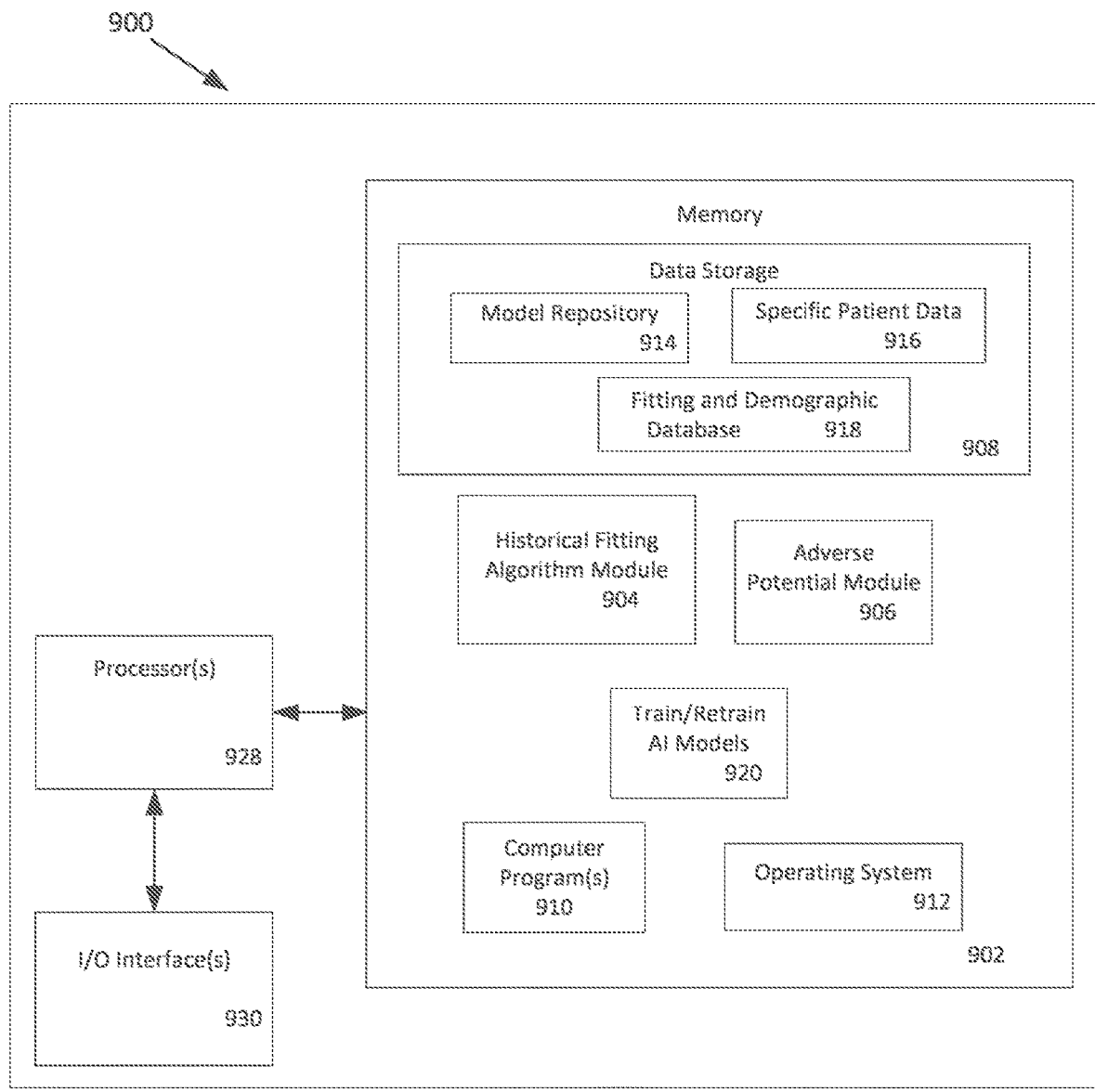
FIG. 9 is a block diagram illustrating an example remote computing device upon which wearable medical device fitting processes may be implemented, in accordance with some implementations.

FIG. 9 shows an example remote computing device 900, such as 130 in FIG. 1, which may implement some of the wearable article matching processes described herein. The remote computer device 900 may include memory 902, processor 928, and I/O interface 930. The various elements of the remote computing device 00 are shown in FIG. 9 as discrete/separate elements for purposes of illustration and explanation. According to some implementations, it is possible to combine some of these elements into a single element or device, while in other implementations of the matching system, these elements may be distributed across a network such as in a cloud computing network. For example, functions of the matching system may be performed by one or both of the multiple remote computing device in a distributed network to provide information to client computing device as a service.

The memory 902 of the remote computing device is for storing information within the remote computing device 900. The types and features of memory 802 of the client computing device described above are applicable to the memory 902 of the remote computing device.

Data store 908 may store various data including AI model training data, specific patient data 916 (which can include LiDAR images, video, photos, spreadsheets, text files, etc.), an AI model repository 914 for storing, aggregating, updating, managing and retrieving the trained AI models applications (e.g. fitting AI model and adverse potential AI model), one or more fitting and demographic database 918 (global previous patient data), and other data. In some implementations, any of the various data may be stored on an external storage rather than in data store 908, and accessed by remote computing device 900.

At least a portion of the information may also be stored on a disk drive or other computer readable storage device (not shown) within the client computing device 800. Such storage device include a floppy disk device, a hard disk device, an optical disk device, or a tape device, digital cards, a flash memory or other similar solid state memory device, or an array of devices.

Various modules or other computer programs 910, also referred to as programs, software, software applications or code, are stored within memory 902 and contain instructions that, when executed, perform one or more methods, such as those described herein. The computer program may be tangibly embodied in an information carrier such as computer or machine readable medium, for example, the memory 902, storage device or memory on processor 928. A machine readable medium is any computer program product, apparatus or device used to provide machine instructions or data to a programmable processor.

An HFA module 904 may accept output results from the fitting AI model and use the output results to select a class of wearable article. The HFA may utilize a wide pool of patient data retrieved and stored. For example, the patient data may include images and multimedia data as well as text and other forms of patient data. An adverse potential module 906 may accept output results from the adverse potential AI model and determine if an actionable adverse potential is detected, and if actionable, may generate an alert accordingly.

One or more train and/or retrain module(s) 920 may be provided to input training or retraining datasets to one or more of the AI models and conduct training or retraining the AI models. However, in some implementations, training and/or retraining or an AI model may be performed by a separate computing system. In these implementations, a fully trained or retrained AI model may be provided by the separate computing system to client computing device 800 for storage and use.

Any suitable programming languages and programming techniques may be used to implement the routines of particular embodiments. Different programming techniques may be employed such as procedural or object-oriented. The routines may execute on a single processing device or multiple processors. Although the steps, operations, or computations may be presented in a specific order, the order may be changed in different particular embodiments. In some particular embodiments, multiple steps shown as sequential in this specification may be performed at the same time. A number of implementations have been described. Features described with conditional language may describe implementations that are optional. The functional blocks, methods, devices, and systems described in the present disclosure may be integrated or divided into different combinations of systems, devices, and functional blocks as would be known to those skilled in the art.

The remote computing device 900 may implement the techniques described herein using customized hard-wired logic, one or more ASICs or FPGAs, firmware and/or program logic which in combination with the computer system causes or programs the client computing device 800 to be a special-purpose machine. According to one implementation, the techniques herein are performed by the client computing device 800 in response to the processor 828 executing one or more sequences of one or more instructions contained in the memory 802. Such instructions may be read into the memory 802 from another storage medium. Execution of the sequences of instructions contained in the memory 802 causes the processor 828 to perform the process steps described herein.

In alternative implementations, one or more methods can be implemented in hardware (logic gates, etc.), or in a combination of hardware and software. Example hardware can be programmable processors (e.g. Field-Programmable Gate Array (FPGA), Complex Programmable Logic Device), general purpose processors, graphics processing units (GPUs), Application Specific Integrated Circuits (ASICs), and the like. One or more methods can be performed as part of or component of an application running on the system, or as an application or software running in conjunction with other applications and operating system 912.

Remote computing device 900 further includes operating system 912. Any operating system 912, e.g., server OS, that is supports the matching processes described herein performed by the remote computing device 900 may be employed.

The processor 928 may process instruction for execution within the client computing device 800 including instructions stored in memory 902 or on the data store 908. The processor 828 may coordinate computing device components, e.g. applications, wireless or wired communication through interfaces, etc. In some implementations, multiple processors and buses may be used.

The processor 928 may be implemented as a chipset of chips that include separate and multiple analog digital processors. The processor may also be implemented using various architectures. For example, the processor 928 may be a CISC (Complex Instruction Set Computer) processor, RISC (Reduced Instruction Set Computer) processor or MISC (Minimal Instruction Set Computer) processor.

The Input/Output (I/O) interface 930 can interface to other input and output devices. In some implementations, the I/O interface 930 can connect to interface devices such as input devices (keyboard, pointing device, touchscreen, microphone, camera, scanner, sensors, etc.) and/or output devices (display devices, speaker devices, printers, motors, etc.). Some implementations can provide a microphone for capturing sound (e.g., as a part of captured images, voice commands, etc.), audio speaker devices for outputting sound, or other input and output devices.

The devices and/or systems described in this document perform functions, processes and/or methods. These functions, processes and/or methods may be implemented by one or more devices that include logic circuitry. Such a device can be alternately called a computer, and so on. It may be a standalone device or computer, such as a general purpose computer, or part of a device that has one or more additional functions. The logic circuitry may include a processor and non-transitory computer-readable storage media, such as memories, of the type described elsewhere in this document. Often, for the sake of convenience only, it is preferred to implement and describe a program as various interconnected distinct software modules or features. These, along with data are individually and also collectively known as software. In some instances, software is combined with hardware, in a mix called firmware.

Moreover, methods and algorithms are described above. These methods and algorithms are not necessarily inherently associated with any particular logic device or other apparatus. Rather, they are advantageously implemented by programs for use by a computing machine, such as a general-purpose computer, a special purpose computer, a microprocessor, a processor such as described elsewhere in this document, and so on.

This detailed description includes flowcharts, display images, algorithms, and symbolic representations of program operations that may be provided within at least one non-transitory, tangible, computer readable medium for execution by the one or more processors. Flowcharts as in FIGS. 3, 4, and 5 are used to describe both programs and also methods. So, while flowcharts described methods in terms of blocks, they also concurrently describe programs.

Other implementations include combinations and sub-combinations of features described or shown in the drawings herein, including for example, implementations that are equivalent to: providing or applying a feature in a different order than in a described implementation, extracting an individual feature from one and inserting such feature into another implementations; removing one or more features from an implementation; or both removing one or more features from an implementation and adding one or more features extracted from one or more other implementations, while providing the advantages of the features incorporated in such combinations and sub-combinations. As used in this paragraph, feature or features can refer to the structures and/or functions of an apparatus, article of manufacture or system, and/or the steps, acts, or modalities of a method.

What is claimed is:

1. A method for selecting a wearable article of a medical device for a patient, the method comprising:
   receiving patient specific data including body measurement data;
   conducting predictive analysis to predict a class of the wearable article that provides a target fit for positioning a component of the wearable article to contact the body of the patient for performance of the medical device to treat and/or monitor the patient for a medical condition, by:
      inputting patient specific data and one or more fit factors to a first artificial intelligence ("AI") model trained on fitting data of previous patients having the same or similar medical condition as the patient; and
      receiving an output from the first AI model that includes a predicted class of wearable article that likely provides the target;
   selecting the class of the wearable article based, at least in part, on the predicted class;
   providing the selected class of the wearable article for treatment and monitoring of the patient for the medical condition during wearing of the wearable article; and
   retraining the first AI model with updated inputs including additional fitting data for new patients fitted with the wearable article.

2. The method of claim 1, wherein the body measurement data is related to a body contact point of the component and is obtained by use of one or more capture devices selected from a group of: a Light Detection and Ranging (LiDAR) device, a body scanner, a camera, a digital scale, and combinations thereof.

3. The method of claim 1, wherein at least a portion of the patient specific data is obtained by a local client computing device and transferred to a remote computing device, wherein the conducting of the predictive analysis and the selecting of the class of the wearable article are performed by the remote computing device.

4. The method of claim 1, wherein the predictive analysis is conducted by a remote computing device, wherein the output result is received by a client computing device, and wherein the selecting of the class of the wearable article is by the client computing device.

5. The method of claim 1, wherein at least a portion of the patient specific data is obtained by a local client computing device, and wherein the conducting of the predictive analysis and the selecting of the class of the wearable article are performed by the client computing device.

6. The method of claim 1, further comprising:
   conducting a second predictive analysis using a second AI model to predict an adverse fit potential of the selected wearable article, by:
      inputting the patient specific data and the selected class of the wearable article to the second AI model, wherein the second AI model is trained using patient experience data in which suboptimal operation of the selected class of wearable article worn by prior patients is due, at least in part, to fit of the wearable article; and
      receiving an output from the second AI model that includes a predicted adverse fit potential; and
   providing an alert of the predicted adverse fit potential to at least one of the patient, a medical provider for the patient, or a caretaker for the patient.

7. The method of claim 1, wherein the patient specific data further includes patient medical condition information.

8. The method of claim 1, wherein the component includes one or more sensors and/or one or more electrodes positioned for cardiac monitoring and treatment by the medical device.

9. The method of claim 1, wherein the retraining of the first AI model includes feeding discrepancy information back into the first AI model, wherein the discrepancy information includes a found adverse effect on the performance of the medical device of previous wearable articles predicted by the first AI model to provide target fit for previous patients.

10. A matching system for selecting a wearable article of a medical device system, the matching system comprising:
   at least one computing device comprising:
      an interface for receiving patient specific data including body measurement data; and
      one or more processors and logic encoded in one or more non-transitory media for execution by the one or more processors and when executed operable to perform steps comprising:
         conducting predictive analysis to predict a class of the wearable article that provides a target fit for positioning a component of the wearable article to contact the body of the patient for performance of the medical device to treat and monitor the patient for a medical condition, by:
            inputting patient specific data and one or more fit factors to a first artificial intelligence ("AI") model trained on fitting data of previous patients having the same or similar medical condition as the patient; and
            receiving an output from the first AI model that includes a predicted class of wearable article that likely provides the target fit; and
            receiving an output from the first AI model that includes a predicted class of the wearable article that likely provides the target fit;
         selecting the class of the wearable article based, at least in part, on the predicted class; and
         providing the selected class of the wearable article for treatment and monitoring of the patient for the medical condition during wearing of the wearable article; and
         retraining the first AI model with updated inputs including additional fitting data for new patients fitted with the wearable article.

11. The system of claim 10, wherein the body measurement data is related to a body contact point of the component and is obtained by use of one or more capture devices selected from a group of: a LiDAR device, a body scanner, a camera, a digital scale, and combinations thereof.

12. The system of claim 10, wherein the at least one computing device includes a local client computing device configured to obtain at least a portion of the patient specific data and to transfer the at least portion of the patient specific data to a remote computing device, and wherein the at least one computing device further includes the remote computing device configured to conduct the predictive analysis and to select the class of the wearable article.

13. The system of claim 10, wherein the at least one computing device includes a remote computing device configured to conduct the predictive analysis, and wherein the at least one computing device further includes a local client computing device configured to receive the output result from the remote computing device and to select the class of the wearable article.

14. The system of claim 10, wherein the at least one computing device includes a local client computing device configured to obtain at least a portion of the patient specific data at a patient location and to transfer the at least portion of the patient specific data to a remote computing device, and wherein the at least one computing device further includes the remote computing device configured to conduct the predictive analysis and transfer the output result to the client computing device, and wherein the client computing device is further configured to select the class of the wearable article.

15. The system of claim 10, wherein the steps further comprise:
    conducting a second predictive analysis using a second AI model to predict an adverse fit potential of the selected wearable article, by:
        inputting the patient specific data and the selected class of the wearable article to the second AI model, wherein the second AI model is trained using patient experience data in which suboptimal operation of the selected class of wearable article worn by prior patients is due, at least in part, to fit of the wearable article; and
        receiving an output from the second AI model that includes a predicted adverse fit potential; and
    providing an alert of the predicted adverse fit potential to at least one of the patient, a medical provider for the patient, or a caretaker for the patient.

16. A method for selecting a wearable article of a medical monitoring device for a patient, the method comprising:
    training a first artificial intelligence ("AI") model by inputting fitting data of previous patients having a medical condition and one or more fit factors for contact of a component of the wearable article with the body of the patient, to predict a class of the wearable article that provides a target fit for positioning a component of the wearable article to contact the body of the patient for performance of the medical device to treat and monitor the patient for the medical condition;
    receiving patient specific data including body measurement data of a patient;
    inputting the patient specific data into the trained first AI model;
    conducting predictive analysis using the trained first AI model to output a predicted class of wearable article that likely provides the target fit based, at least in part, on the patient specific data as input to the first AI model;
    selecting the class of the wearable article based, at least in part, on an output result of the predictive analysis to provide the selected class of the wearable article for treatment and monitoring of the patient during wearing of the wearable article;
    determining that the selected class of the wearable article fails to provide the target fit for the patient; and
    generating discrepancy data to feed back into the trained first AI model for retraining; and
    retraining the first AI model with updated inputs including additional fitting data for new patients fitted with the wearable article.

17. The method of claim 16, further comprising:
    training a second AI model using patient experience data of previous patients to predict an adverse fit potential of the selected wearable article for the patient in which suboptimal operation of the selected class of wearable article worn by prior patients is due, at least in part, to fit of the wearable article;
    inputting the patient specific data into the trained second AI model;
    conducting a second predictive analysis using the trained second AI model to output a predicted adverse fit potential of the selected wearable article, based on the patient specific data and the selected class of the wearable article class;
    determining that the selected class of the wearable article causes an adverse experience for the patient; and
    generating discrepancy data to feed back into the trained second AI model for retraining.

* * * * *